United States Patent [19]

Beug et al.

[11] Patent Number: 5,792,645

[45] Date of Patent: Aug. 11, 1998

[54] PROTEIN-POLYCATION NUCLEIC ACID COMPLEXES AND METHODS OF USE

[75] Inventors: Hartmut Beug; Max L. Birnstiel; Matthew Cotten, all of Vienna; Ernst Wagner, Langenzersdorf, all of Austria

[73] Assignee: Boehringer Ingelheim International GmbH, Germany

[21] Appl. No.: 254,888

[22] Filed: Jun. 6, 1994

Related U.S. Application Data

[62] Division of Ser. No. 492,460, Mar. 9, 1990, Pat. No. 5,354,844.

[30] Foreign Application Priority Data

Mar. 16, 1989 [AT] Austria ............................. A 610/89

[51] Int. Cl.[6] ........................... C12N 5/16; C12N 15/87; C12Q 1/68; C07K 17/06
[52] U.S. Cl. ................... 435/240.2; 435/6; 435/69.1; 435/91.1; 435/91.3; 435/91.31; 435/91.4; 435/172.3; 536/23.1; 536/24.5; 536/25.1; 536/25.3; 514/44; 530/345; 530/358; 530/395; 530/400; 530/402
[58] Field of Search ............................. 514/44; 536/24.5, 536/23.1, 25.1, 25.3; 435/69.1, 70.1, 70.3, 70.4, 91.1, 91.21, 91.3, 91.31, 91.4, 172.3, 6, 240.2; 530/345, 358, 395, 400, 402; 935/52, 55, 56, 57

[56] References Cited

U.S. PATENT DOCUMENTS

| | | | |
|---|---|---|---|
| 5,087,616 | 2/1992 | Myers et al. | 514/21 |
| 5,166,320 | 11/1992 | Wu et al. | 530/395 |
| 5,354,844 | 10/1994 | H. Beug et al. | 530/345 |
| 5,521,291 | 5/1996 | Curiel et al. | 530/391.7 |
| 5,547,932 | 8/1996 | Curiel et al. | 435/65 |

FOREIGN PATENT DOCUMENTS

| | | | |
|---|---|---|---|
| 0 153 151 | 8/1985 | European Pat. Off. | A61K 37/02 |
| WO 88/00837 | 2/1988 | WIPO | A61K 47/00 |
| WO 88/05077 | 7/1988 | WIPO | C12N 15/00 |

OTHER PUBLICATIONS

O. Shohat et al. Oncogene, vol. 1 ('87) pp. 277–283.

J. Haseloff et al. Nature, vol. 334 (18 Aug. 1988) pp. 585–591.

P. Zamecnik et al. PNAS, vol. 75 #1 (Jan. '78) pp. 280–284.

C. Fromentol et al. Cell, vol. 54 (Sep. 23, 1988) pp. 943–953.

P. Westermann et al. Biomed. Biochim. Acta, vol. 48, #1 ('89) pp. 85–93.

R. Weiss Science News, vol. 139 (16 Feb. '91) pp. 108–109.

M. Barinaga Science, vol. 262 (3 Dec. '93) pp. 1512–1514.

W. James Antiviral Chemistry & Chemotherapy, vol. 2#4 ('91) pp. 191–214.

R. Mulligan, Science, vol. 260 (14 May 1993) pp. 926–932.

E. Uhlmann et al. Chemical Reviews. vol. 90 #4 (Jun. 1990) pp. 543–584.

B. Tseng et al. Cancer Gene Therapy, vol. 1 #1 (Mar. 1994) pp. 65–71.

C. Stein et al., Science, vol. 261 (20 Aug. 1993) pp. 1004–1012.

Ascoli & Puett, "Tritium Labeling of Luteinizing Hormone by Reductive Methylation," *Biophys. Acta* 371:203–210 (1974).

Beug et al., "Erythroblast Cell Lines Transformed by a Temperature-Sensitive Mutant of Avian Erythroblastosis Virus: A Model System To Study Erythroid Differentiation In Vitro," *J. Cell. Physiol. Suppl.* 1:195–207 (1982).

Beug et al., "Hormone–Dependent Terminal Differentiation in Vitro of Chicken Erythroleukemia Cells Transformed by ts Mutants of Avian Erythroblastosis Virus," *Cell* 28:907–919 (Apr. 1982).

Beug & Hayman, "Temperature–Sensitive Mutants of Avian Erythroblastosis Virus: Surface Expression of the erbB Product Correlates with Transformation,"*Cell* 36:963–972 (April 1984).

Cormier & Ogilvie, "Synthesis of hexanucleotide analogues containing diisopropylsilyl internucleotide linkages," *Nucl. Acids Res.* 16:4853–4594 (1988).

Cotten et al., "Transferrin–polycation–mediated introduction of DNA into human leukemic cells: stimulation by agents that affect the survival of transfected DNA or modulate transferrin receptor levels," *Proc. Natl. Acad. Sci. USA* 87:4033–4037 (Jun. 1990).

Deakin et al., "'Glucose 6–Phosphate–Dehydrogenase' Activity and Thiol Content of Thymus Nuclei from Control and X–Irradiated Rats," *Biochem. J.* 89:296–304 (1963).

European Search Report Application 90104700.1.

Felsenfeld, G., "Chromatin," *Nature* 271:115–122 (Jan. 12, 1978).

Graf et al., "Temperature–sensitive mutant of avian erythroblastosis virus suggests a block of differentiation as mechanism of leukaemogenesis," *Nature* 275:496–501 (Oct. 12, 1978).

Huebers & Finch, "The Physiology of Transferrin and Transferrin Receptors," *Physiol. Rev.* 67:520–582 (Apr. 1987).

(List continued on next page.)

*Primary Examiner*—Charles C.P. Rories
*Attorney, Agent, or Firm*—Sterne, Kessler, Goldstein & Fox P.L.L.C.

[57] ABSTRACT

The invention relates to a system for transporting nucleic acids into the cell, which is effected by receptor-mediated endocytosis. Using a transferrin-polycation conjugate, a complex can be formed with the polyanionic nucleic acid. This complex is bound to the transferrin receptor, which is highly regulated in growing cells, and absorbed into the cell. Suitable nucleic acids include those which inhibit specific genes or the RNA function, such as antisense oligonucleotides or ribozymes or the genes coding for them. The invention further relates to a process for introducing nucleic acids into the cells, transferrin-polycation/nucleic acid complexes and pharmaceutical preparations containing them.

20 Claims, 13 Drawing Sheets

OTHER PUBLICATIONS

Jung et al., "Biological Activity of the Antitumor Protein Neocarzinostatin Coupled to a Monoclonal Antibody by N–Succinimidyl 3–(2–Pyridyldithio)–Propionate," *Biochem. & Biophys. Res. Comm.* 101:599–606 (Jul. 30, 1981).

Khazaie et al., "Truncation of the human EGF receptor leads to differential transforming potentials in primary avian fibroblasts and erythroblasts," *EMBO J.* 7:3061–3071 (1988).

Kohgo et al., "Kinetics of Internalization and Cytotoxicity of Transferrin–Neocarzinostatin Conjugate in Human Leukemia Cell Line, K562," *Jpn. J. Cancer Res.* 81:91–99 (Jan. 1990).

Lemaitre et al., "Specific antiviral activity of a poly(L–lysine)–conjugated oligodeoxyribonucleotide sequence complementary to vesicular stomatitis virus N protein mRNA initiation site," *Proc. Natl. Acad. Sci. USA* 84:648–652 (Feb. 1987).

Mahler & Cordes, in: *Bioligical Chemistry*, Harper & Row Publishers, New York, pp. 53–54 (1966).

Morvan et al., "α–DNA VII. Solid phase synthesis of α–anomeric oligodeoxyribonucleotides," *Nucl. Acids Res.* 16:833–847 (1988).

Nolan et al., "Fluorescence–activated cell analysis and sorting of viable mammalian cells based on β–D–galactosidase activity after transduction of *Escherichia coli lacZ*," *Proc. Natl. Acad. Sci. USA* 85:2603–2607 (Apr. 1988).

Orkin et al., "Differentiation in Erythroleukemic Cells and Their Somatic Hybrids," *Proc. Natl. Acad. Sci. USA* 72:98–102 (Jan. 1975).

Praseuth et al., "Sequence–specific binding and photocrosslinking of α and β oligodeoxynucleotides to the major groove of DNA via triple–helix formation," *Proc. Natl. Acad. Sci. USA* 85:1349–1353 (Mar. 1988).

Radke et al., "Transformation of Both Erythroid and Myeloid Cells by E26, an Avian Leukemia Virus That Contains the myb Gene," *Cell* 31:643–653 (Dec. 1982).

Schmidt et al., "Control of Erythroid Differentiation: Possible Role of the Transferrin Cycle," *Cell* 46:41–51 (Jul. 4, 1986).

Shen, W.C., "Acid–sensitive dissociation between poly(l-ysine) and histamine–modified poly(glutamate) as a model for drug–releasing from carriers in endosomes," *Biochem. Biophys. Acta* 1034:122–124 (Apr. 23, 1990).

Smith et al., "Antiviral effect of an oligo(nucleoside methylphosphonate) complementary to the splice junction of herpes simplex virus type 1 immediate early pre–mRNAs 4 and 5," *Proc. Natl. Acad. Sci. USA* 83:2787–2791 (May 1986).

Stavridis & Psallidopoulos, "Use of Transferrin as a Gene–Carrier to the Erythroid Cells of the Marrow," *Cell. & Mol. Biol.* 28:15–18 (1982).

Stein et al., "Complete Inhibition of Transferrin Recycling by Monensin in K562 Cells," *J. Biol. Chem.* 259:14762–14772 (Dec. 10, 1984).

Stein et al., "Physicochemical properties of phosphorothioate oligodeoxynucleotides," *Nucl. Acids Res.* 16:3209–3221 (1988).

Stirchak & Summerton, "Uncharged Stereoregular Nucleic Acid Analogues. 1. Synthesis of a Cytosine–Containing Oligomer with Carbamate Internucleoside Linkages," *J. Org. Chem.* 52:4202–4206 (1987).

Wagner et al., "Transferin–polycation conjugates as carriers for DNA uptake into cells," *Proc. Natl. Acad. Sci. USA* 87:3410–3414 (May 1990).

Warrant & Kim, "α–Helix–double helix interaction shown in the structure of a protamine–transfer RNA complex and a nucleoprotamine model," *Nature* 271:130–135 (Jan. 12, 1978).

Wienhues et al., "A Novel Method for Transfection and Expression of Reconstituted DNA–Protein Complexes in Eukaryotic Cells," *DNA* 6:81–89 (1987).

Wu & Wu, "Receptor–mediated in vitro gene transformation by a soluble DNA carrier system," *J. Biol. Chem.* 262:4429–4432 (Apr. 5, 1987).

Wu & Wu, "Receptor–mediated Gene Delivery and Expression in Vivo," *J. Biol. Chem.* 263:14621–14624 (Oct. 15, 1988).

Zamecnik et al., "Inhibition of replication and expression of human T–cell lymphotropic virus type III in cultured cells by exogenous synthetic oligonucleotides complementary to viral RNA," *Proc. Natl. Acad. Sci. USA* 83:4143–4146 (Jun. 1986).

Zenke et al., "v–erbA Specifically Suppresses Transcription of the Avian Erythrocyte Anion Transporter (Band 3) Gene, " *Cell* 52:107–119 (1988).

Zenke et al., "Receptor–mediated endocytosis of transferrin–polycation conjugates: an efficient way to introduce DNA into hematopoietic cells," *Proc. Natl. Acad. Sci. USA* 87:3655–3659 (May 1990).

Zon, G., "Oligonucleotide Analogues as Potential Chemotherapeutic Agents," *Pharmaceutical Res.* 5:539–549 (1988).

T 1 2 3 4 5 6

T 1 2 3 4 5 6

Tf A B C D

Tf A B C D

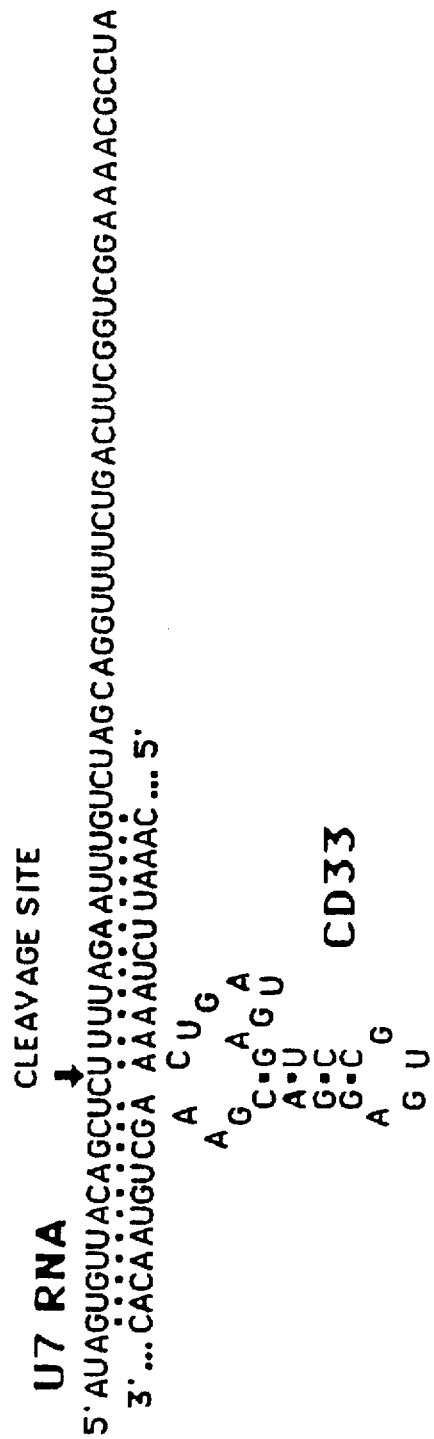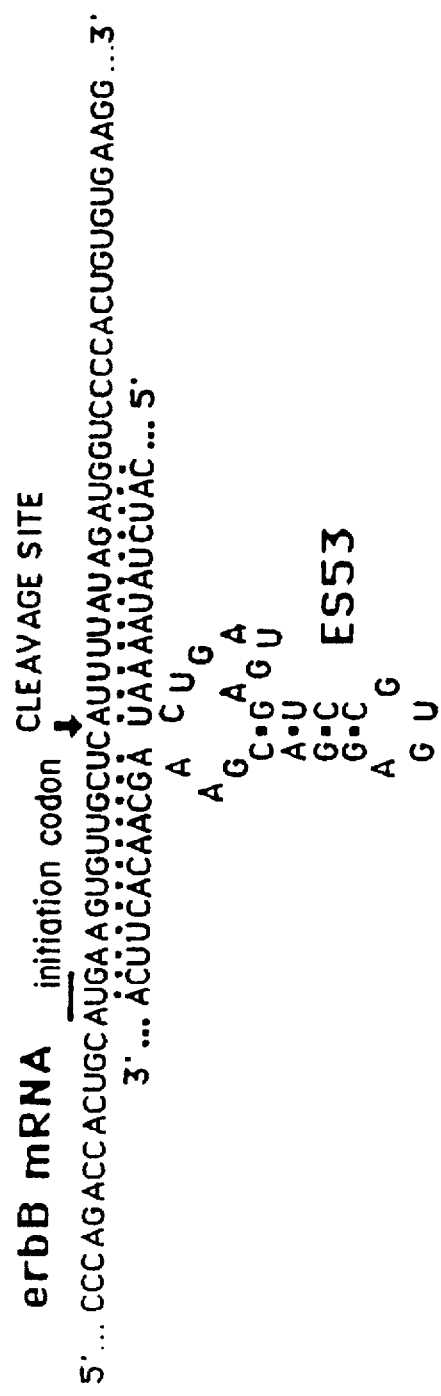
FIG. 11A
FIG. 11B

PROTEIN-POLYCATION NUCLEIC ACID COMPLEXES AND METHODS OF USE

This application is a division. of application Ser. No. 07/492.460. filed Mar. 9, 1990, now U.S. Pat. No. 5,354,.

FIELD OF THE INVENTION

The invention relates to the transporting of substances with an affinity for polycations, particularly nucleic acids, into the cell, the transportation being carried out by means of receptor-mediated endocytosis.

BACKGROUND OF THE INVENTION

Antisense RNAs and DNAs have proved to be effective agents for selectively inhibiting certain genetic sequences in cell-free systems as well as within the living cell. Their mode of activity is based on the specific recognition of a complementary nucleic acid strand and attachment thereto, thus affecting the transcription, translation and cleaving processes. This mechanism of activity theoretically makes it possible to use antisense oligonucleotides as therapeutic agents which will block the expression of certain genes (such as deregulated oncogenes or viral genes) in vivo. It has already been shown that short antisense oligonucleotides can be imported into cells and perform their inhibiting activity therein (Zamecnik et al., 1986), even though the intracellular concentration thereof is low, partly because of their restricted uptake through the cell membrane owing to the strong negative charge of the nucleic acids.

Another method of selectively inhibiting genes consists in the application of ribozymes, i.e. RNA molecules which recognise specific RNA sequences and are able to bind to them and cleave them. Here again there is the need to guarantee the highest possible concentration of active ribozymes in the cell, for which transportation into the cell is one of the limiting factors.

In order to counteract this limiting factor, a number of solutions have already been proposed.

One of these solutions consists in direct modification of nucleic acids, e.g. by substituting the charged phosphodiester groups with uncharged methyl phosphonates (Smith et al., 1986), carbamates (Stirchak et al., 1987) or silyl compounds (Cormier et al., 1988) or using phosphorothioates (Stern et al., 1988). Another possible method of direct modification consists in the use of nucleoside analogues (Morvan et al., 1988, Praseuth et al., 1988)).

Even though some of these proposals appear to offer a promising way of solving the problem, they do have numerous disadvantages, e.g. reduced binding to the target molecule and a reduced inhibitory effect. A chief disadvantage of the in vivo use of modified oligonucleotides is the possible toxicity of these compounds.

An alternative method to the direct modification of the oligonucleotides consists in leaving the oligonucleotide itself unchanged and providing it with a group which will impart the desired properties to it, e.g. with molecules which will make transportation into the cell easier. One of the proposed solutions within the scope of this principle consists in conjugating the oligonucleotide with polycationic compounds (Lemaitre et al.. 1987).

Various techniques are known for genetic transformation of mammalian cells in vitro, but the use of these techniques in vivo is restricted (these include the introduction of DNA by means of viruses, liposomes, electroporation, microinjection, cell fusion, DEAE dextran or the calcium phosphate precipitation method).

Attempts have therefore already been made to develop a soluble system which can be used in vivo, which will convey DNA into the cells in a directed manner by means of receptor-mediated endocytosis (G. Y. Wu, C. H. Wu, 1987). This system was developed for hepatocytes and is based essentially on the following two facts:

1. On the surface of the hepatocytes there are receptors which bind specific glycoproteins and convey them into the cell.
2. DNA can be bound to polycationic compounds, e.g. polylysine, by a strong electrostatic interaction, forming soluble complexes.

The system is based on the principle of coupling polylysine with a glycoprotein of a kind to which the receptor will respond and then, by adding DNA, forming a soluble glycoprotein/polylysine/DNA complex which will be transported to the cells containing the glycoprotein receptor and, after the absorption of the complex into the cell, will make it possible for the DNA sequence to be expressed.

SUMMARY OF THE INVENTION

The objective of the present invention was to provide a highly active transporting system which is more widely applicable than the known system, which can only be used for one particular cell type owing to the specific presence of the receptor on this one cell type.

According to the invention, the solution to the problem consists in the fact that the polycation is bound to transferrin.

(A) Hemoglobin content of cells grown in the presence of no additives (triangles); in the presence of iron-saturated conalbumin (circles); and in the presence of iron-saturated TfpL 270 (squares). The shaded area shows the hemoglobin content of cells grown without transferrin.

(B) Hemoglobin content of cells grown in the presence of iron-saturated conalbumin (open circles); TfpL 90 (open squares) and TfpL 270 (solid squares).

Figure 7A:
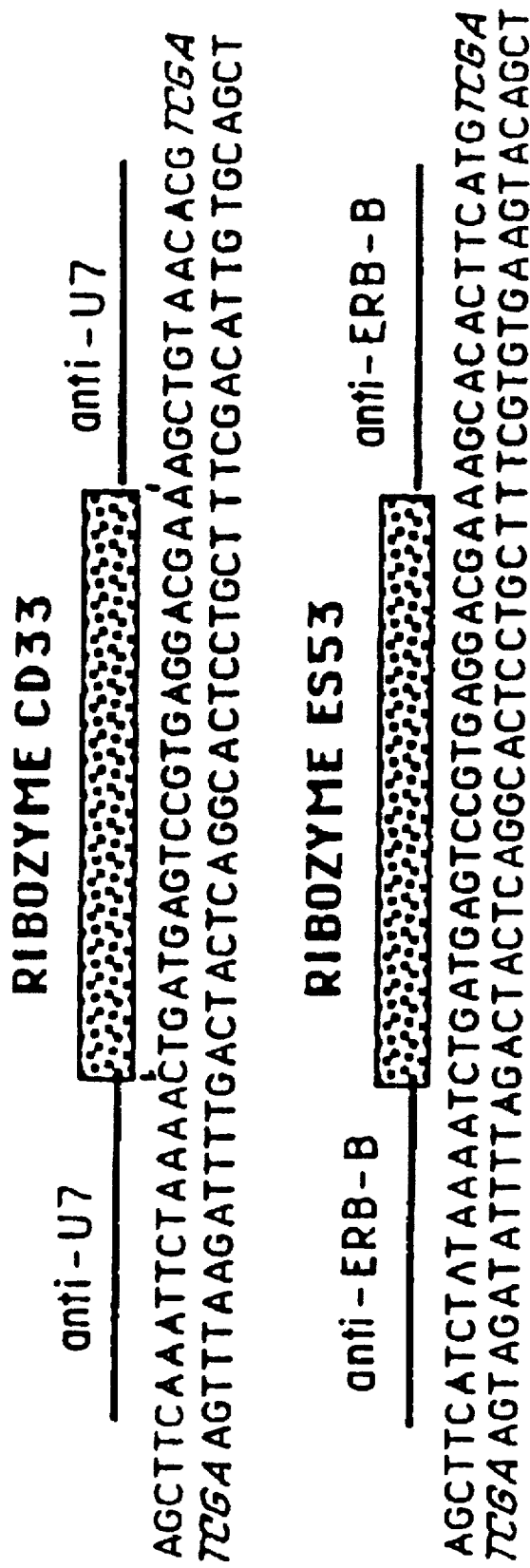
Figure 7B:
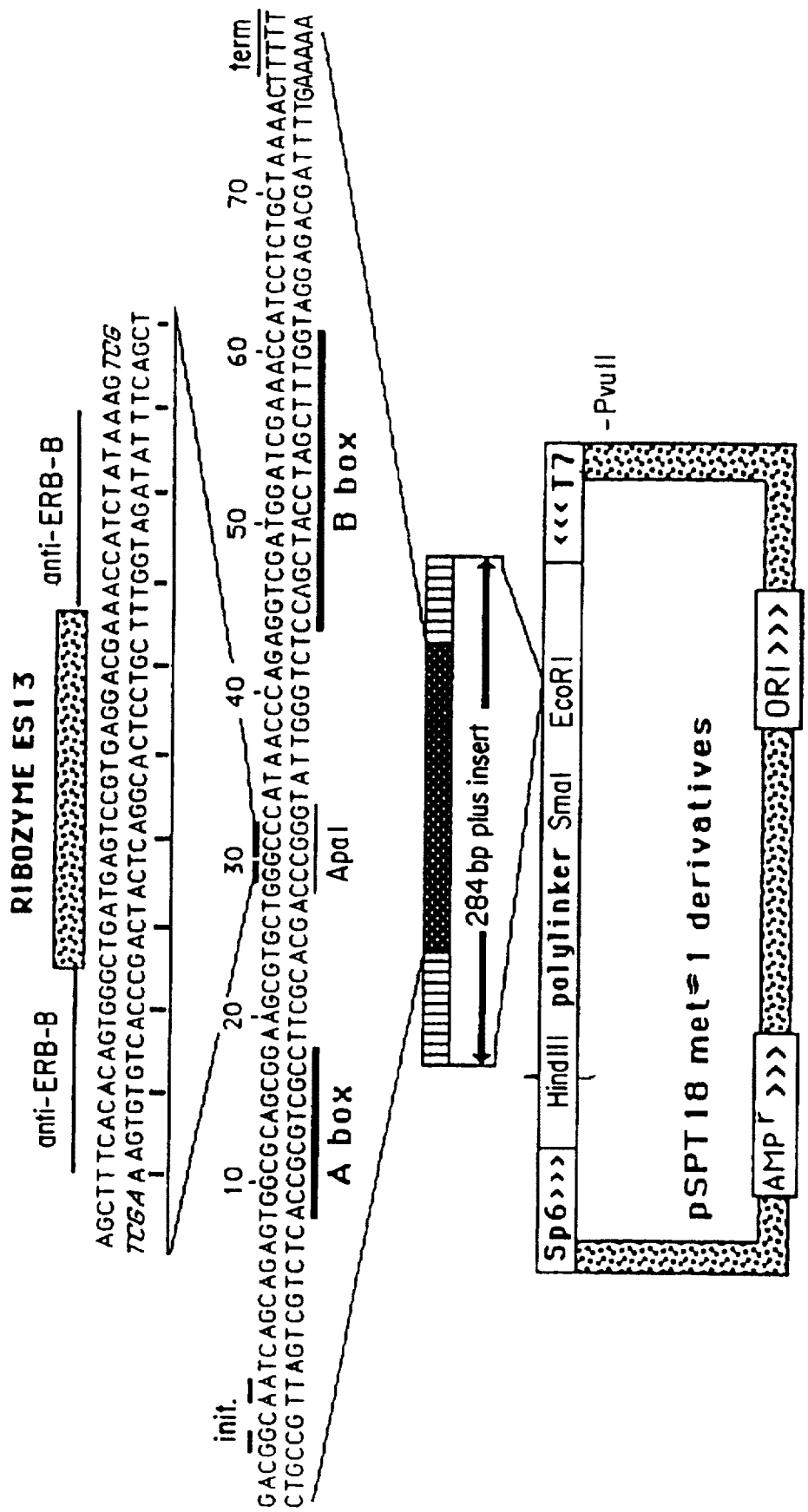

FIG. 7. Structure of transported DNA in comparison with tDNA ribozymes.

Figure 8:
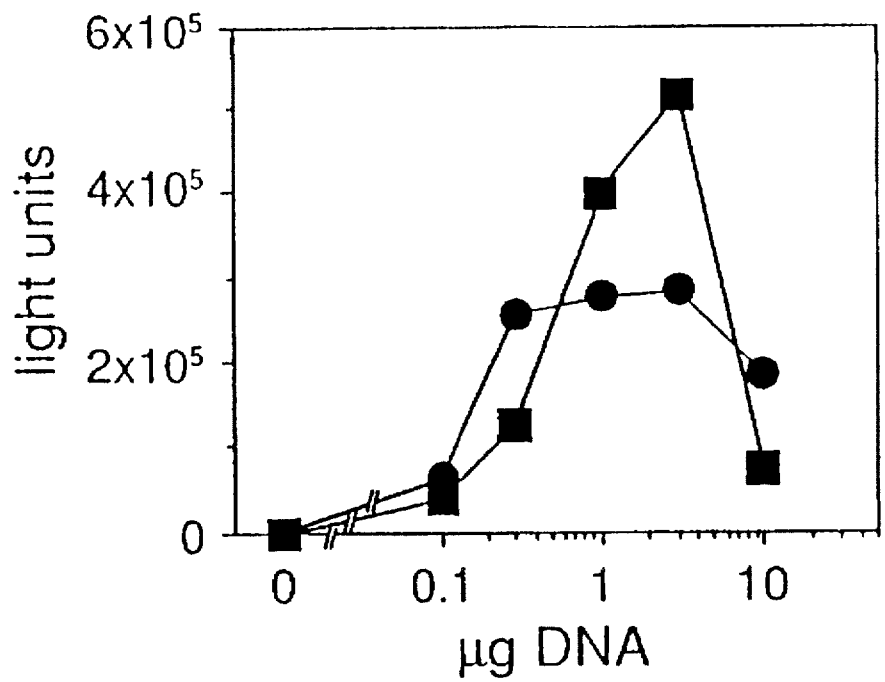

FIG. 8. Absorption of plasmid-DNA into chicken erythroblasts using polylysine-transferrin conjugates. (Circles: Tfprot; Squares: TfpL.)

Figure 9:
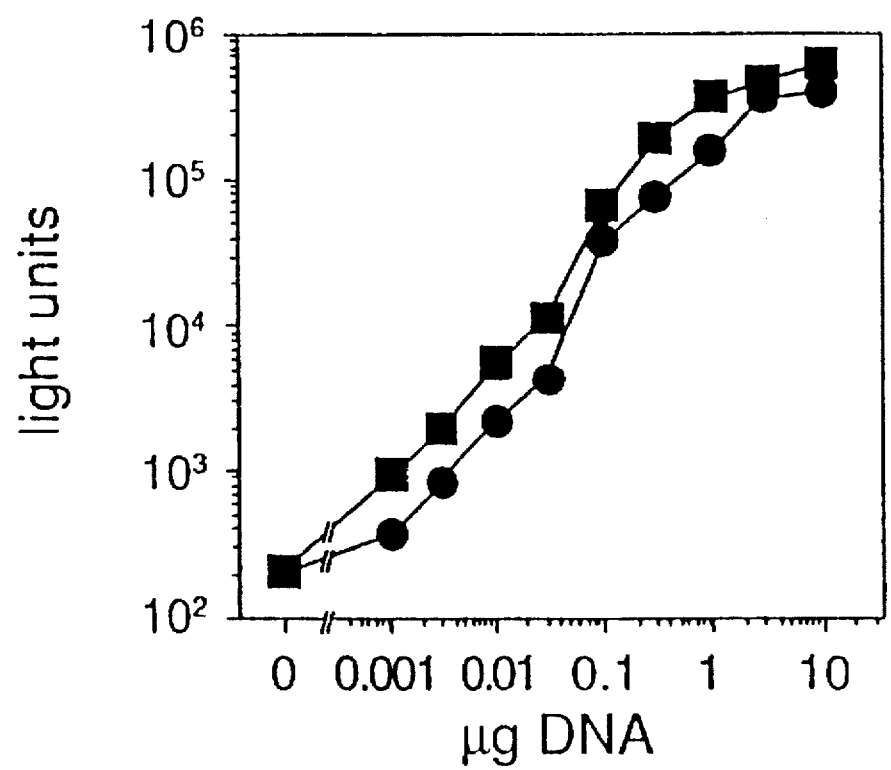

FIG. 9. Absorption of DNA into chicken erythroblasts using polylysine-transferrin conjugates. (Circles: Tfprot; Squares: TfpL.)

Figure 10A:
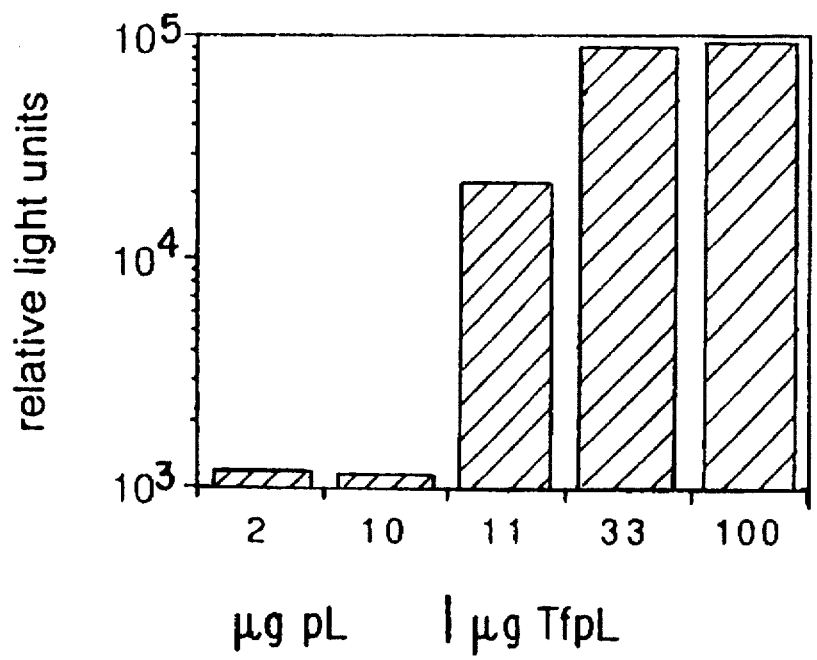
Figure 10B:
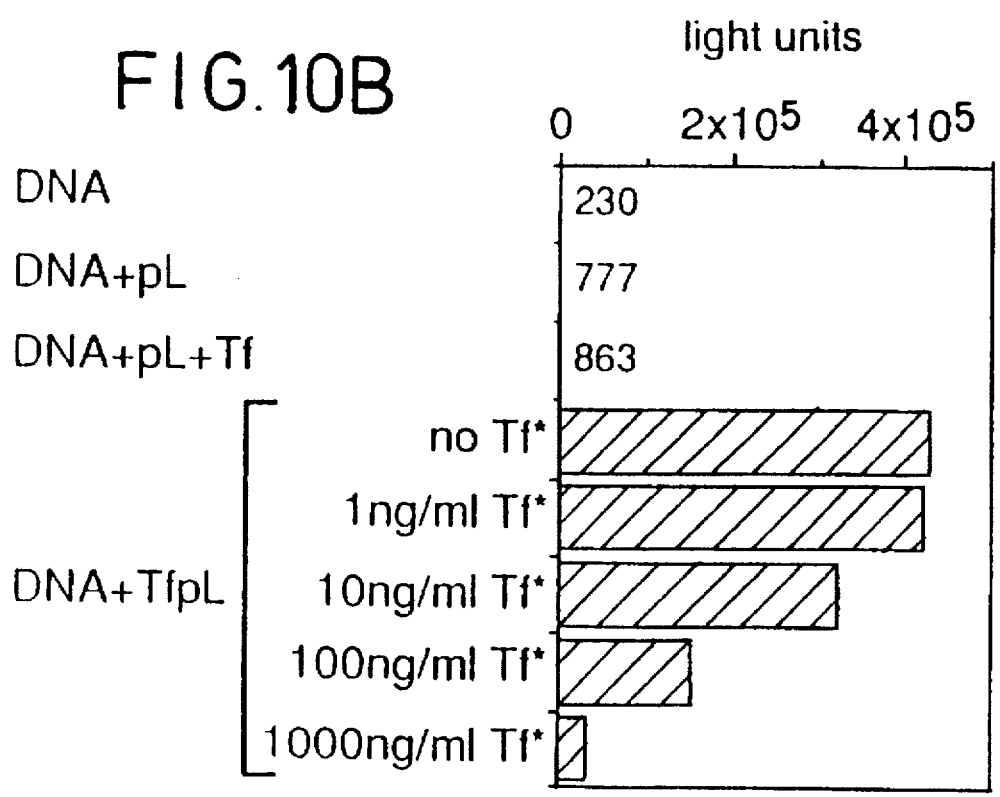

FIGS. 10A and 10B. Absorption of transferrin-polycation/DNA complexes into cells is effected via transferrin receptors.

(A) Luciferase activity achieved for pL-DNA complexes and TfpL-DNA complexes.

(B) Free transferrin in medium competes for DNA uptake mediated by TfpL.

Figure 11C:
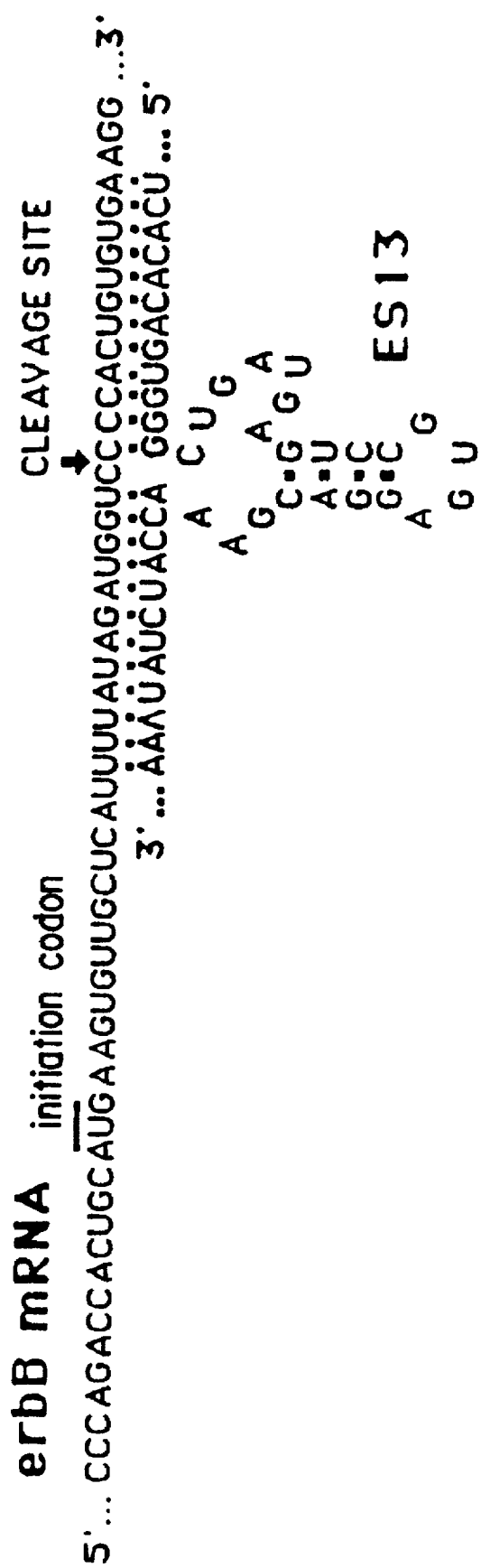

FIG. 11(A–C). Structure of tRNA ribozyme genes directed against translation initiation region of erbB.

Figure 12:
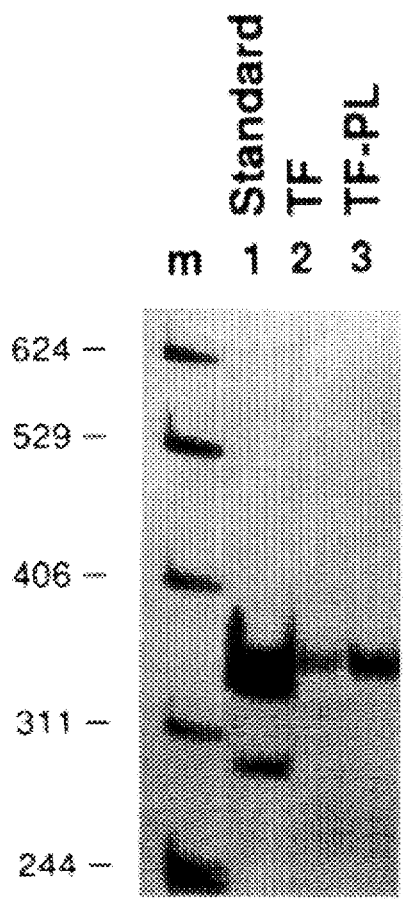

FIG. 12. Absorption of DNA by cells treated with transferrin-polylysine/DNA:

Trace m: molecular weight marker: pBR322 DNA, cleaved with HpaII and radioactively labelled using the Klenow fragment of DNA polymerase with alpha-$^{32}$P-CTP.

Trace 1: 2000 cpm ES13 fragment.

Trace 2: material from cells treated with transferrin and ES13.

Trace 3: material from cells treated with transferrin-polylysine and ES13.

Figure 13:
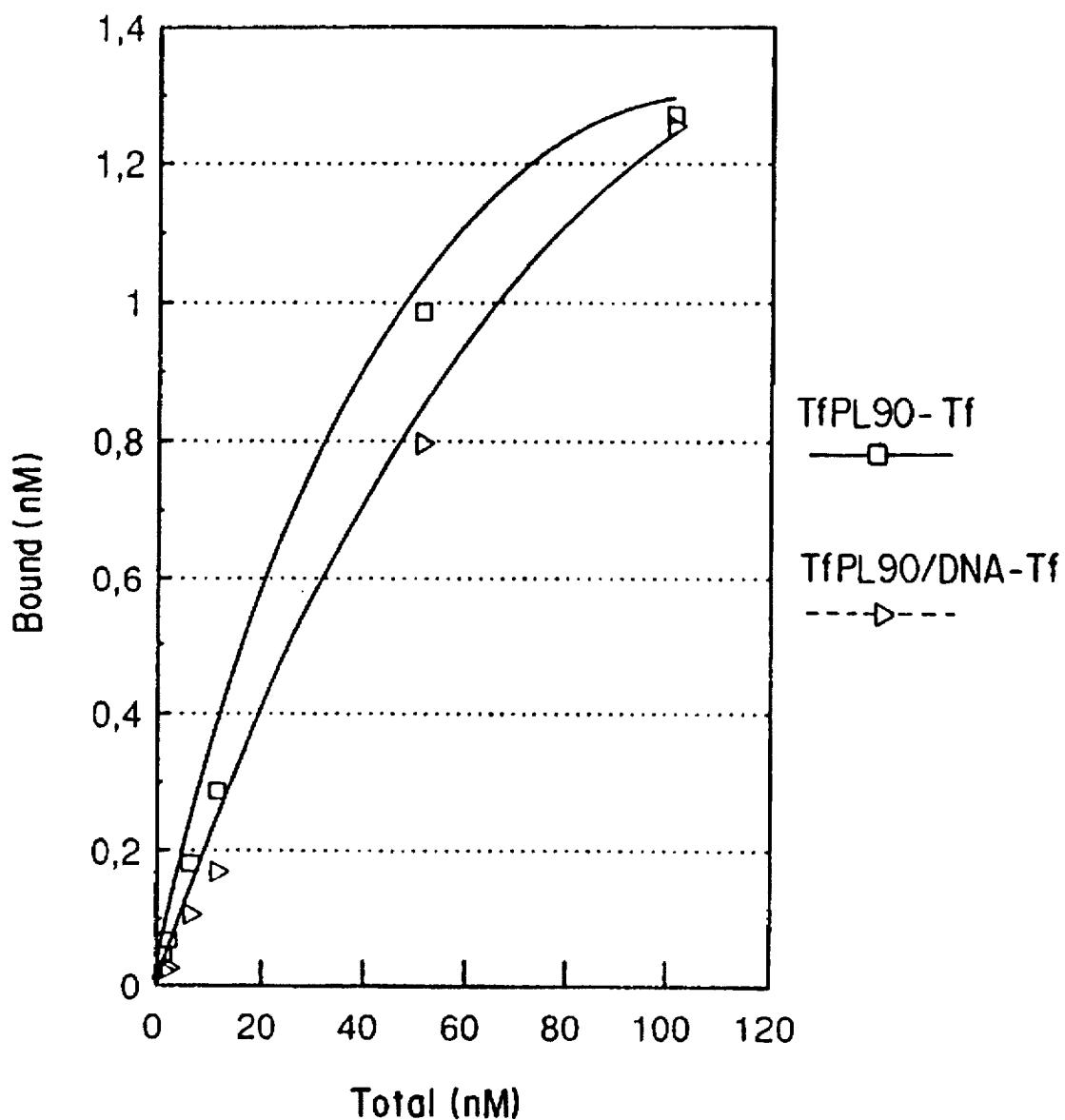

FIG. 13. Binding and internalization of transferrin-polylysine/DNA complexes in hemopoietic chicken cells. Labelled TfpL 90 (squares) or labelled TfpL 90 complexed with DNA (triangles) bound to HD3 cells in such a way that saturation occurs.

Figure 14:
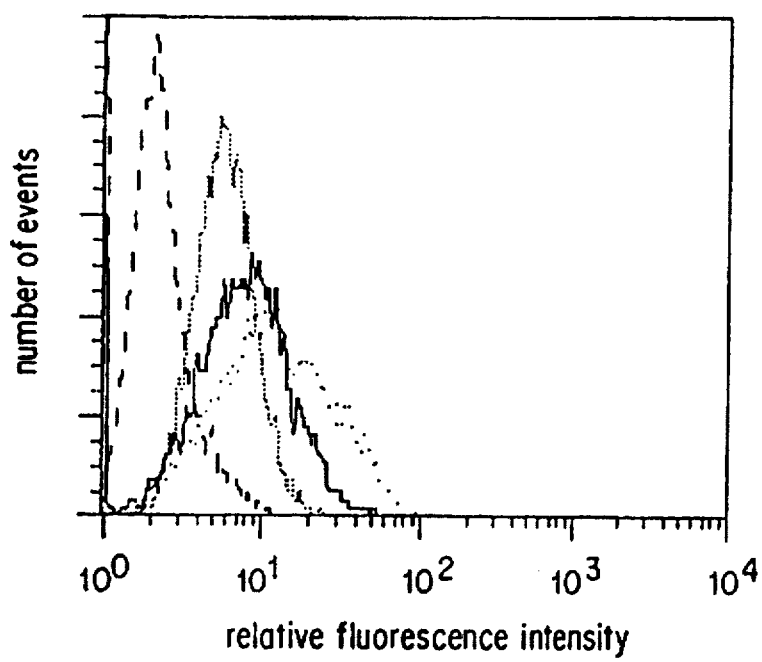

FIG. 14. Uptake of TfpL conjugate and TfpL-DNA complex by cells. Cells were incubated with Tf ( . . . ); TfpL ( . . . ); TfpL/DNA (__); binding buffer ( . . . ).

Figure 15:
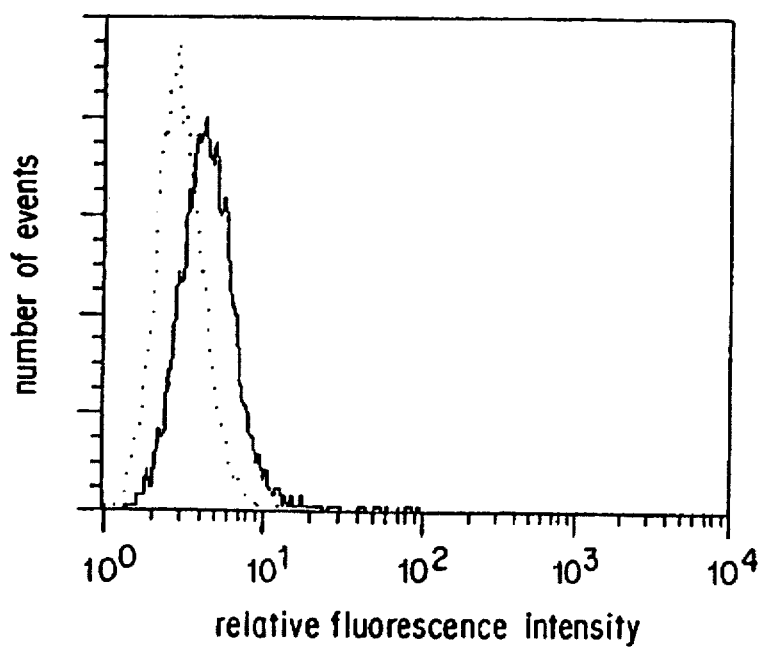

FIG. 15. Uptake of TfpL/DNA complexes (using pRSV-βGal plasmid DNA) by HD3 cells. Cells were incubated with TfpL-pB-SK-DNA ( . . . ) or with TfpL-pRSV-βGal-DNA (__). The fluorescent βGal substrate FDG was introduced by osmotic shock.

DETAILED DESCRIPTION OF THE INVENTION

Transferrins are a class of related metal-binding transporting glycoproteins with an in vivo specificity for iron. Various mammalian transferrins have been identified, plasma transferrin supplying the majority of body tissue with iron. The main producer of transferrin is the liver.

Transferrin has a molecular weight of about 80,000, 6% of which consists of the sugar residues. A transferrin molecule is able to bind two molecules of iron, and this binding requires the presence of carbonate or bicarbonate ions.

The transferrin receptor, which occurs in a number of forms which possibly deviate slightly from one another on the various cells (e.g. in the carbohydrate group) is a transmembrane glycoprotein with a molecular weight of about 180,000, whilst a receptor molecule is able to bind one or possibly two molecules of transferrin.

At the physiological pH of 7.4, the transferrin receptor has a very high affinity for $Fe_2$ transferrin, lower affinity for the Fe transferrin and virtually no affinity for apotransferrin, even though the latter forms a very stable complex with the receptor at a pH of about 5.

Transferrin receptors have been detected in particularly large numbers in precursors of erythrocytes, placenta and liver and in measurable amounts in a number of other body tissues. A particularly interesting observation is that the receptor is highly regulated in growing cells. It has also been observed that the number of receptors is substantially increased in neoplastic tissue in vivo compared with benign lesions, indicating an increased iron requirement. The absorption mechanism of the transferrin-iron complex by receptors and the intracellular cycle thereof have been thoroughly researched.

There is still no absolute certainty as to the exact sequence of events of the release of the iron molecules by transferrin, although the majority view is that the molecules are released mainly intracellularly. In a process which is dependent on energy and temperature, Fe transferrin or $Fe_2$ transferrin is bound to the receptor on the cell membrane. Then the complex is absorbed into a vesicle, referred to as endosome or receptosome. This is combined with another vesicle having a pH of <5.5; the resulting acidification causes the iron to be released by the transferrin. The apotransferrin receptor complex is then transported back to the cell membrane, where the neutral pH causes the apotransferrin to be released from the receptor into the surrounding medium. There are indications that the recycling, the functioning of which is based on the affinity of the receptor for apo- or iron transferrin, which varies at acid and neutral pH values, takes place through vesicles of the Golgi apparatus.

At a molecular level, the initiation of the transferrin cycle has not yet been explained; there are merely indications regarding some aspects, e.g. the possible role of phosphorylation (Huebers et al., 1987).

With the present invention it has been possible for the first time to make use of this active transporting system in order to convey into the cell nucleic acids, the absorption of which runs into difficulties.

The present invention thus relates to new protein-polycation conjugates which are capable of forming complexes with substances having an affinity for polycations, particularly nucleic acids or nucleic acid analogues, and these complexes are absorbed into the cell by means of receptor-mediated endocytosis, the protein content of the conjugate being transferrin.

It has been found, surprisingly, that nucleic acids can be efficiently transported into the cell whilst maintaining their inhibitory activity, using the conjugates according to the invention.

The word "transferring" in accordance with this invention relates to both the natural transferrins and also to transferrin modifications which are bound by the receptor and transported into the cell (such modifications may consist, for example, of a change in the amino acids or a shortening of the molecule to the fraction which is responsible for receptor binding).

The molar ratio of transferrin to polycation is preferably 10:1 to 1:4, whilst it should be borne in mind that aggregates may be formed. However, this ratio may if necessary be within wider limits, provided that it satisfies the condition that complexing of the nucleic acid or acids takes place and it is ensured that the complex formed-will be bound by the transferrin receptor and conveyed into the cell; this can easily be checked by simple experiments carried out from one case to the next.

The ratio chosen will depend particularly on the size of the polycation molecule and the number and distribution of the positively charged groupings, these criteria being matched to the size and structure of the nucleic acid or acids to be transported and to any modifications thereto. The polycations may be identical or different.

The following compounds may be used as polycations:

a) Protamines: these are small (MW up to about 8000) strongly basic proteins, the positively charged amino acid groups of which (especially arginines) are usually arranged in groups and neutralise the negative charges of nucleic acids because of their polycationic nature (Warrant et al., 1978). The protamines which may be used within the scope of the present invention may be of natural origin or produced by recombinant methods, whilst multiple copies may be produced or modifications may be made in the molecular size and amino acid sequence. Corresponding compounds may also be chemically synthesised. When an artificial protamine is synthesised the procedure used may consist, for example, in replacing amino acid residues, which have functions in the natural protamine which are undesirable for the transporting function (e.g. the condensation of DNA) with other suitable amino acids, and/or at one end providing an amino acid (e.g. cysteine) which will enable the desired conjugation with transferrin.

b) Histones: these are small DNA-binding proteins present in the chromatin, having a high proportion of positively charged amino acids (lysine and arginine) which enable them to bind to DNA independently of the nucleotide sequence and fold it into nucleosomes, the arginine-rich histones H3 and H4 being particularly suitable (Felsenfeld, 1978). As for the preparation and modifications thereof, the remarks made above in relation to protamines apply here as well.

c) Synthetic polypeptides such as homologous polypeptides (polylysine, polyarginine) or heterologous polypeptides (consisting of two or more representatives of positively charged amino acids).

d) Non-peptide cations such as polyethyleneimines.

The size of the polycations is preferably selected so that the sum of the positive charges is about 20 to 500 and this is matched to the nucleic acid which is to be transported.

The transferrin-polycation conjugates according to the invention may be produced chemically or, if the polycation is a polypeptide, by the recombinant method. Coupling by the chemical method can be carried out in a manner known per se for the coupling of peptides and if necessary the individual components may be provided with linker substances before the coupling reaction (this procedure is necessary when there is no functional group suitable for coupling available at the outset, such as a mercapto or alcohol group). The linker substances are bifunctional compounds which are first reacted with functional groups of the individual components, after which coupling of the modified individual components is carried out.

Depending on the desired properties of the conjugates, particularly the desired stability thereof, coupling may be carried out by means of a) disulphide bridges, which can be cleaved again under reductive conditions (e.g. using succinimidyl pyridyl dithiopropionate (Jung et al., 1981)).

b) Using compounds which are largely stable under biological conditions (e.g. thioethers, by reacting maleimido linkers with sulfhydryl groups of the linker bound to the second component).

c) Using bridges which are unstable under biological conditions, e.g. ester bonds, or using acetal or ketal bonds which are unstable under weakly acidic conditions.

The production of the conjugates according to the invention by the recombinant method offers the advantage of producing precisely defined, uniform compounds, whereas chemical coupling produces conjugate mixtures which then have to be separated.

The recombinant preparation of the conjugates according to the invention can be carried out using methods known for the production of chimeric polypeptides. The polycationic peptides may vary in terms of their size and amino acid sequence. Production by genetic engineering also has the advantage of allowing the transferrin part of the conjugate to be modified, by increasing the ability to bind to the receptor, by suitable mutations, for example, or by shortening the transferrin fraction to the part of the molecule which is responsible for the binding to the receptor. It is particularly expedient for the recombinant preparation of the conjugates according to the invention to use a vector which contains the sequence coding for the transferrin part as well as a polylinker into which the required sequence coding for the polycationic peptide is inserted. In this way, a set of express plasmids can be obtained, of which the plasmid containing the desired sequence can be used as necessary in order to express the conjugate according to the invention.

The nucleic acids which are to be transported into the cell may be DNAs or RNAs, with no restrictions as to the nucleotide sequence. The nucleic acids may be modified, provided that this modification does not affect the polyanionic nature of the nucleic acids; these modifications include, for example, the substitution of the phosphodiester group by phosphorothioates or the use of nucleoside analogues.

Nucleic acids which may be used within the scope of the present invention include particularly those which are to be transported into the cell for the purpose of inhibiting specific gene sequences. These include antisense oligonucleotides and ribozymes, optionally together with a carrier nucleic acid. With regard to the size of the nucleic acids the invention again permits a wide range of uses. There is no lower limit brought about by the transporting system according to the invention; any lower limit which might arise would be for reasons specific to the application, e.g. because antisense oligonucleotides with less than about 10 nucleotides would hardly be suitable owing to their lack of specificity. Using the conjugates according to the invention it is also possible to convey plasmids into the cell, the smaller plasmids which are used as carrier nucleic acids (e.g. retroviral vectors with up to 5000 bp) being of particular practical use. It is also possible to convey different nucleic acids into the cell at the same time using the conjugates according to the invention.

A further advantage of the present invention is the fact that there are polymorphisms for transferrin and the receptor which can be exploited for the deliberate transporting of inhibiting nucleic acids into specific cells.

Within the scope of the present invention it has been possible to demonstrate that transferrin-polycation conjugates can be efficiently absorbed into living cells and internalised. The conjugates or complexes according to the invention are not harmful to cell growth. This means that they can be administered repeatedly and thus ensures a constantly high expression of genes inserted into the cell.

It has also been possible to show that the polycation-transferrin conjugates can functionally replace the native transferrin-iron complex. The fact that the transferrin-polycation/DNA complexes are absorbed through the cell by means of the transferrin receptor has been confirmed using the luciferase gene as DNA component. It has been shown that native transferrin efficiently displaces the transferrin-polycation/DNA complex, and this has been measured by the reduction in the luciferase activity in the cell.

The experiments carried out within the scope of this invention have also demonstrated that a tRNA ribozyme gene (the ribozyme being directed against a V-erbB sequence) can be introduced into erbB-transformed chicken cells using a conjugate according to the invention (polylysine-transferrin) and can attenuate the transforming activity of the oncogene. This result is all the more significant as only a small amount of ribosome gene was used in these experiments.

The ratio of nucleic acid to conjugate can vary within a wide range, and it is not absolutely necessary to neutralise all the charges of the nucleic acid. This ratio will have to be adjusted for each individual case depending on criteria such as the size and structure of the nucleic acid which is to be transported, the size of the polycation and the number and distribution of its charges, so as to achieve a ratio of transportability and biological activity of the nucleic acid which is favourable to the particular application. This ratio can first of all be adjusted coarsely, for example by using the delay in the speed of migration of the DNA in a gel (e.g. using the mobility shift on an agarose gel) or by density gradient centrifugation. Once this provisional ratio has been obtained, it may be expedient to carry out transporting tests with the radioactively labelled complex with respect to the maximum available activity of the nucleic acid in the cell and then reduce the proportion of conjugate if necessary so that the remaining negative charges of the nucleic acid are not an obstacle to transportation into the cell.

The preparation of the transferrin-polycation/nucleic acid complexes, which are also a subject of the invention, can be carried out using methods known Per se for the complexing of polyionic compounds. One possible way of avoiding uncontrolled aggregation or precipitation is to mix the two components together first of all at a high (about 1 molar) concentration of common salt and subsequently to adjust to physiological saline concentration by dialysis or dilution. Preferably, the concentrations of DNA and conjugate used in the complex forming reaction are not too high (more than 100 µg/ml), to ensure that the complexes are not precipitated.

The preferred nucleic acid component of the transferrin-polycation-nucleic acid complex according to the invention is antisense-DNA, antisense-RNA or a ribozyme or the gene coding for it. When ribozymes and antisense-RNAs are used it is particularly advantageous to use the genes coding for these RNAs which inhibit the function of RNA, preferably together with a carrier gene. By introducing the gene into the cell, a substantial amplification of the RNA is ensured, as against the importing of RNA as such, and consequently a sufficient amount to inhibit the biological reaction is ensured. Particularly suitable carrier genes are the transcription units, e.g. tRNA genes, required for transcription by polymerase III. Ribozyme genes, for example, may be inserted into them in such a way that when the transcription is carried out the ribozyme is part of a compact polymerase III transcript. Using the transporting system according to the present invention it is possible to intensify the activity of these genetic units, by guaranteeing an increased initial concentration of the gene in the cell.

The invention further relates to a process for introducing nucleic acid or acids into human or animal cells, preferably forming a complex which is soluble under physiological conditions.

The invention further relates to pharmaceutical preparations containing as the active component a nucleic acid which specifically inhibits a gene, complexed with a transferrin-polycation conjugate, e.g. in the form of a lyophilisate. Such pharmaceutical preparations may be used to inhibit pathogenic viruses such as HIV or related retroviruses, oncogenes or other key genes which control growth and/or differentiation of cells, e.g. the c-fos gene or the c-myc gene, together with antisense oligonucleotides, antisense oligonucleotide analogues or ribozymes or the DNAs coding for them, optionally together with a carrier nucleic acid, in humans or animals.

Another field of use is in fighting diseases by inhibiting the production of undesirable gene products, e.g. the major plaque protein which occurs in Alzheimer's disease or proteins which cause autoimmune diseases.

The invention is illustrated by means of the Examples which follow.

EXAMPLE 1

Preparation of transferrin-polylysine 90 conjugates

Coupling was carried out using methods known from the literature (Jung et al., (1981)) by introducing disulphide bridges after modification with succinimidyl-pyridyl dithiopropionate.

a) 3-(2-Pyridyldithio)propionate-modified transferrin 6 ml of a solution, gel-filtered over Sephadex G-25, of 120 mg (1.5 µmol) of transferrin (from chicken albumin, Sigma, Conalbumin Type I, iron-free) in 3 ml of 0.1M sodium phosphate buffer (pH 7.8) were mixed with 200 µl of 15 mM ethanolic solution of succinimidyl 3-(2-pyridyldithio)propionate (3 µM, SPDP, Pharmacia) with vigorous shaking and the mixture was left to react for 1 hour at ambient temperature with occasional shaking. Low molecular reaction products and traces of reagent were removed using a gel column (Sephadex G-25, 14×180 mm, 0.1M sodium phosphate buffer pH 7.8) and 7 ml of the product fraction were obtained; the content of pyridyl dithiopropionate residues bound to transferrin was determined by means of one aliquot, after reduction with dithiothreitol, by photometric measurement of the quantity of pyridin-2-thione released and the result was 2.6 µmol. Human transferrin (Sigma, iron-free) was modified in exactly the same way.

b) Mercaptopropionate-modified polylysine 90 (pL 90)

A solution of 18 mg (about 1.0 µmol) of poly(L)lysine-hydrobromide (Sigma, fluoresceinisothio-cyanate (=FITC)-labelled, molecular weight of about 18,000—corresponding to an average degree of polymerisation of about 90) in 3 ml of 0.1M sodium phosphate (pH 7.8) was filtered over Sephadex G-25 (the fluorescent labelling was carried out in sodium bicarbonate buffer pH 9 for 3 hours). The polylysine solution was diluted with water to 7 ml, combined with 270 µl of a 15 mM ethanolic solution of SPDP with thorough shaking and then left to react for 1 hour in the dark at ambient temperature and with occasional shaking. After the addition of 0.5 ml of 1M sodium acetate buffer (pH 5.0) the mixture was filtered over Sephadex G-25 to separate off any lower molecular substances (eluant: 20 mM sodium acetate buffer pH 5.0). The product fraction (ninhydrin staining, fluorescence) was evaporated down in vacuo, adjusted to pH about 7 with buffer, a solution of 23 mg (150 µmol) of dithiothreitol in 200 µl of water was added and the mixture was left to stand for 1 hour in the dark under argon at ambient temperature. Excess reducing agent was separated off by further gel filtration (Sephadex G-25, 14×130 mm column, 10 mm sodium acetate buffer pH 5.0) and 3.5 ml of product solution of fluorescently labelled polylysine were obtained, containing 3.8 µmol of mercapto groups (photometric determination using Ellman's reagent, 5,5'-dithiobis(2-nitrobenzoic acid).

c) Transferrin-polylysine conjugates

Figure 1:
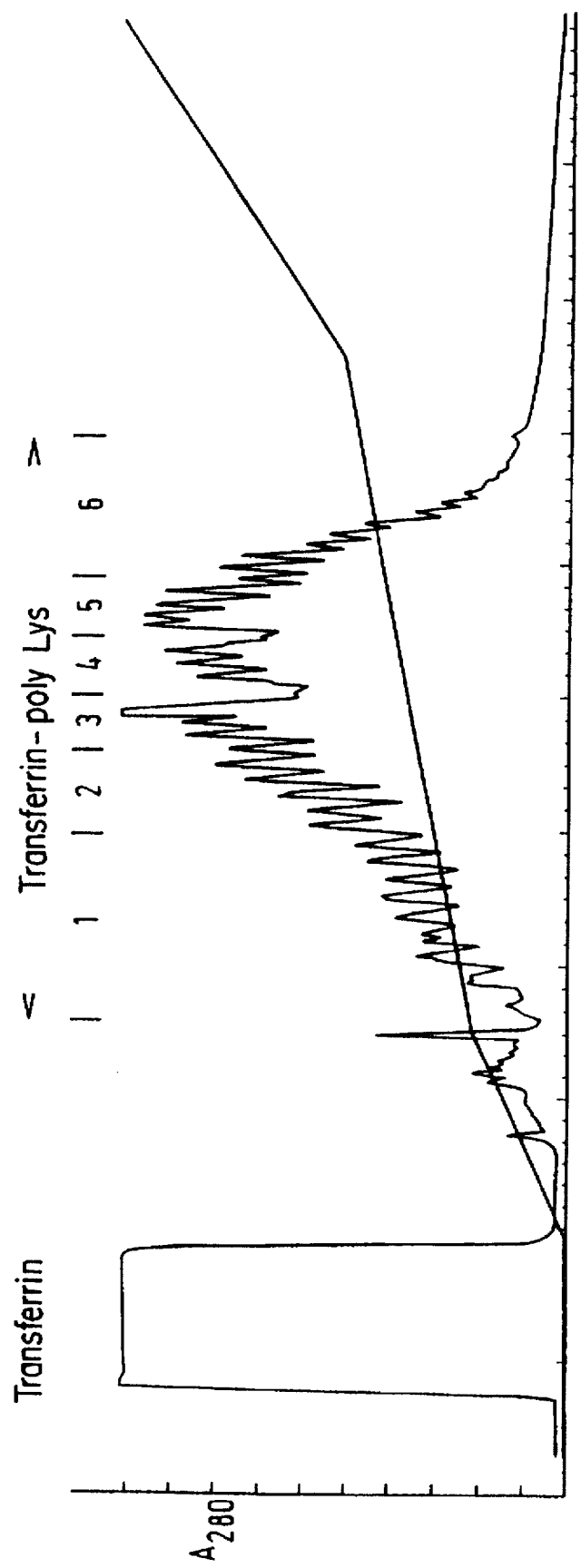
FIG. 1. Ion exchange gradient separation of non-conjugated transferrin from transferrin-polylysine conjugates.

The solution of modified transferrin obtained in a) (7 ml in 0.1M sodium phosphate buffer pH 7.8, about 1.5 µmol transferrin with about 2.6 µmol pyridyl dithiopropionate residues) was rinsed with argon; 2.0 ml of the solution of mercapto-modified polylysine obtained in b) (in 10 mm sodium acetate buffer pH 5.0, corresponding to about 0.6 µmol of polylysine with about 2.2 µmol of mercapto groups) were added, the mixture was rinsed with argon, shaken and left to react for 18 hours at ambient temperature in the dark and under argon. The reaction mixture was diluted with water to 14 ml and separated by ion exchange chromatography (Pharmacia Mono S column HR 10/10, gradient elution, buffer A: 50 mM HEPES pH 7.9, buffer B: A+3M sodium chloride, 0.5 ml/min, FIG. 1). Non-conjugated transferrin was eluted at the start, product fractions at about 0.66–1.5M sodium chloride.

Averaged over all the fractions, conjugates were obtained containing a ratio of transferrin to polylysine of 1.3:1.

The conjugated products (ninhydrin staining, in UV at 280 nm protein absorption, and fluorescence measurement of FITC-labelled polylysine at 495 nm) were collected in 6 fractions each containing about 10 mg of transferrin. The fractions were first dialysed against a 100 mm iron(III) citrate solution (adjusted to pH 7.8 with sodium hydrogen carbonate) and then twice more with 1 mM HEPES buffer (pH 7.5).

Figure 2B:
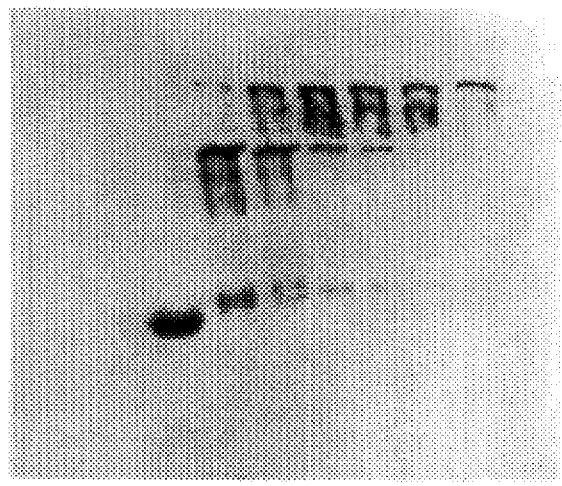
FIG. 2A and B. SDS gel electrophoresis showing an approximately equal content of transferrin in transferrin 1-polylysine conjugate fractions after pre-treatment with 2-mercaptoethanol. 2B. In unreduced samples there were no visible bands for transferrin, only less widely migrating conjugates. (T=untreated transferrin; 1–6=conjugate fractions 1–6.)
Figure 2A:
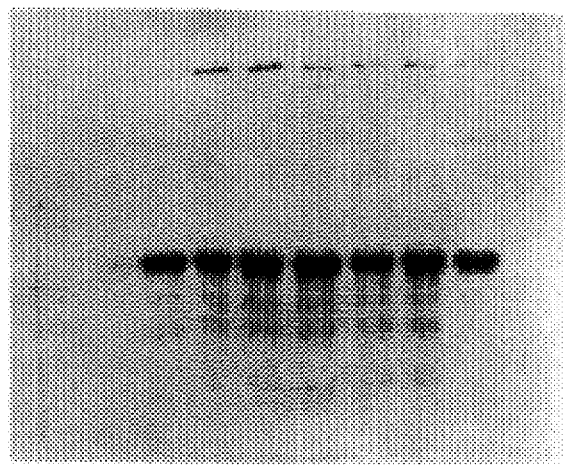

Sodium dodecylsulphate gel electrophoresis (10% SDS, 8% polyacrylamide), see FIG. 2, showed an approximately equal content of transferrin in all 6 fractions after pretreatment with 2-mercaptoethanol (FIG. 2A), whereas in the unreduced samples there were no visible bands for free transferrin, only less widely migrating conjugates (FIG. 2B, T=untreated transferrin; 1–6=conjugate fractions 1–6).

EXAMPLE 2

Preparation of transferrin-polylysine 270 and transferrin-polylysine 450 conjugates (pL270 and pL450)

a) Modified transferrin was produced analogously to Example 1 a)

b) Preparation of modified polylysine 270 and polylysine 450

A gel-filtered solution of 0.33 µmol polylysine 270 (with an average degree of polymerisation of 270 lysine groups, with or without fluorescent labelling; corresponding to 19 mg of hydrobromide salt) in 1.2 ml of 75 mM sodium acetate buffer was adjusted to pH 8.5 by the addition of sodium carbonate buffer. 182 µl of a 15 mM ethanolic solution of SPDP (1.9 µmol) was added with vigorous stirring. One hour later, 200 µl 1M sodium acetate pH 5 were added; after gel filtration with 20 mM sodium acetate, a solution was obtained containing 0.27 µmol of polylysine 270 with 1.3 µmol mercapto groups (4.8 linkers per polylysine chain). Analogously, 0.20 µmol of polylysine 450 (with an average degree of polymerisation of 450 lysine groups) were modified with 2.25 µmol of SPDP, obtaining a product of 0.19 µmol polylysine 450 with 2.1 µmol mercapto groups (11 linkers per polylysine chain). Analogously to Example 1 b), the dithiopyridine groups were reduced with dithiothreitol, in order to obtain the free sulfhydryl components.

c) Preparation of transferrin-polylysine conjugates

Transferrin-polylysine 270 conjugates were prepared by mixing 1.0 µmol of modified transferrin in 100 mM phosphate buffer, pH 7.8, with 0.14 µmol of modified polylysine 270 (in 20 mM sodium acetate buffer) with the exclusion of oxygen in an argon atmosphere. After 18 hours at ambient temperature the reaction mixture was diluted with water to a volume of 10 ml and separated by cation exchange chromatography (Pharmacia Mono S column HR 10/10; gradient elution, buffer A: 50 mM HEPES pH 7.9; buffer B: A+3M sodium chloride; UV absorption at 280 nm and fluorescence measurement, excitation 480 nm, emission 530 nm). The excess of non-coupled transferrin was eluted first; the product fractions were eluted at between 30% and 50% gradient B and pooled in 3 conjugate fractions (molar ratios of transferrin to polylysine: pool A: 5.5 to 1; pool B: 3.4 to 1; pool C: 1.8 to 1). The conjugates were obtained in an average yield of 0.23 µmol transferrin with 0.075 µmol of polylysine 270.

Transferrin-polylysine 450 conjugates were prepared in a similar manner, starting from 1.2 µmol of modified transferrin according to Example 1 a) (in 20 mM HEPES pH 7.9 containing 80 mM sodium chloride) and 71 nmol of mercapto-modified polylysine 450 according to Example 2 b) in acetate buffer.

The reaction mixture was purified by gel permeation chromatography (Pharmacia Superose 12 column, 1M guanidine chloride pH 7.3) and after dialysis (20 mM HEPES pH 7.3, containing 100 mM sodium chloride) yielded transferrin-polylysine-conjugates containing 0.40 µmol of transferrin with 38 nmol of polylysine 450.

Iron was incorporated by adding 6–12 µl of 100 mM iron citrate buffer (containing sodium bicarbonate adjusted to pH 7.8) to the samples, per mg of transferrin fraction.

EXAMPLE 3 a) Preparation of transferrin-protamine conjugates
Modified transferrin was prepared as in Example 1 a).

b) Preparation of 3-mercaptopropionate-modified protamine

To a solution of 20 mg (3 µmol) of protamine trifluoracetate salt (prepared by ion exchange chromatography from salmon protamine (=salmin)–sulphate, Sigma) in 2 ml of DMSO and 0.4 ml of isopropanol, containing 2.6 µl (15 µmol) of ethyl diisopropylamine, was added a solution of 30 µmol of SPDP in 250 µl of isopropanol and 250 µl of DMSO in several batches over a period of one hour. After 3.5 hours at ambient temperature the solution was evaporated down under high vacuum and taken up in 0.5% acetic acid containing 10% methanol. Gel filtration (Sephadex G10; 0.5% acetic acid with 10% methanol) yielded, after lyophilisation, 16 mg (2.5 µmol of protamine acetate salt, modified with 2.5 µmol of dithiopyridine linker. Reduction of 1.75 µmol of protamine (containing 1.75 µmol of linker) with 16 mg of dithiothreitol in sodium bicarbonate buffer, pH 7.5, for 1 hour under argon, followed by adjustment of the pH to 5.2 and gel filtration over Sephadex G10 with 20 mM sodium acetate buffer, pH 5.2, yielded a protamine solution modified with 1.6 µmol of mercaptopropionate linker.

c) Preparation of transferrin-protamine conjugates

Figure 3A:
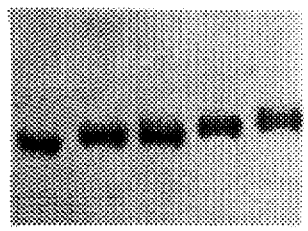
FIG. 3 (panels (A) and (B)). Preparation of transferrin-protamine conjugates. The transferrin-protamine conjugate fractions A–D are more slowly migrating bands on SDS gel electrophoresis (A), whereas in β-mercaptoethanol-reduced samples only the transferrin band was visible (B).
Figure 3B:
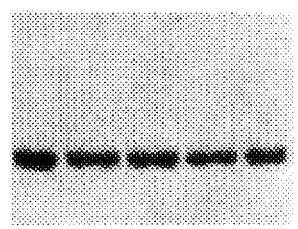

The reaction of the protamine solution obtained in b) (1.6 µmol linker) with 1.34 µmol of transferrin (modified with 3.1 µmol of dithiopyridine linker) and subsequent purification by cation exchange chromatography as described for transferrin-polylysine conjugates, yielded four product fractions A–D eluted one after the other, containing 90, 320, 240 and 120 nMol, respectively, of modified transferrin with increasing amounts of protamine (determined by SDS gel electrophoresis; 10% SDS, 8% polyacrylamide, Coomassie blue staining). FIG. 3 shows the results of the SDS gel electrophoresis. The Tfprot conjugate fractions A–D more slowly migrating bands (a), whereas in β-mercaptoethanol-reduced samples (b) only the transferrin band was visible. Dialysis and the incorporation of iron were carried out as described for the transferrin-polylysine conjugates TfpL270 and TfpL450 in Example 2.

EXAMPLE 4

Preparation of complexes of transferrin-polycation conjugates with DNA

Figure 4:
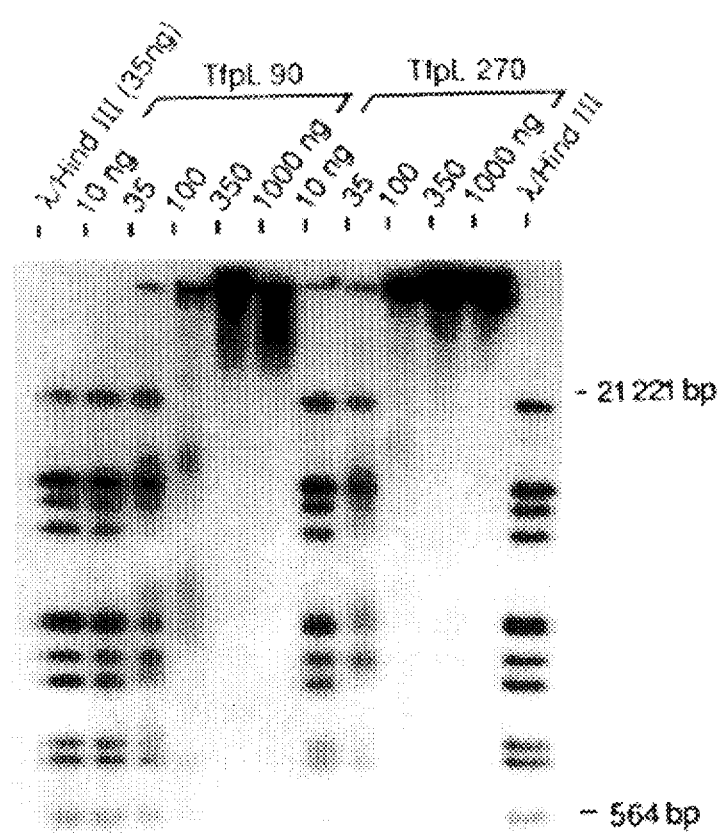
FIG. 4. Binding of transferrin-polycation conjugates with DNA was confirmed using a gel mobility shift assay using $^{32}$P-labelled lambda DNA cut with Eco R1/Hind III.

The complexes were prepared by mixing dilute solutions of DNA (30 µg/ml or less) with the transferrin-polycation conjugates. In order to prevent precipitation of the DNA complexes, phosphate-free buffer was used (phosphates reduce the solubility of the conjugates). The binding of the DNA to the polycation conjugates under physiological ionic conditions was confirmed by a gel mobility shift assay using lambda DNA $^{32}$P-labelled at the 3'-end, cut with EcoR 1/Hind III (FIG. 4). To each sample of 1 µl (35 ng) of DNA were added 3 µml of a 100 mM HEPES buffer pH 7.9, containing 1M sodium chloride, and the samples were mixed with increasing amounts (10 ng to 1000 ng) of transferrin conjugates in 11 µl of aqueous solution, resulting in a final concentration of sodium chloride of 200 mM. Electrophoresis on a 1% agarose gel with 1×TAE eluting buffer was carried out at 50 Volts (45 mA) for 2.5 hours; the gel was dried, followed by autoradiography for 2 hours at −80° C. using an XAR film (Kodak).

EXAMPLE 5

Transporting of transferrin-polylysine conjugates into living cells

In order to demonstrate that the transferrin-polylysine conjugates described in Example 1 are efficiently absorbed into living erythroblasts, FITC-labelled conjugates were used. It is known (Schmidt et al. 1986) that FITC-labelled transferrin was detectable in vesicles inside the cell (when examined under a fluorescence microscope) after some hours' incubation with erythroblasts from which transferrin had previously been removed.

Figure 5A:
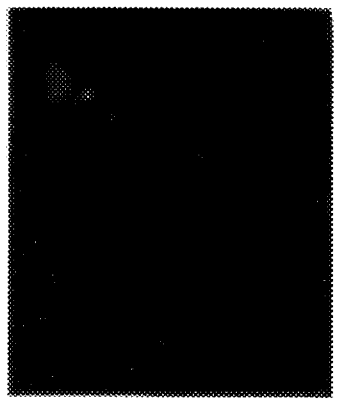
FIG. 5 (panels A, B and C). Fluorescence images of chicken erythroblasts incubated for 24 hours without (A) or with (B, C) FITC-labelled transferrin-polylysine conjugates.
Figure 5B:
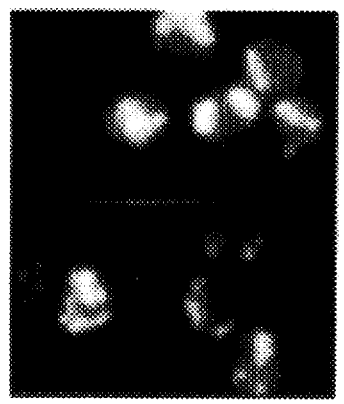
Figure 5C:
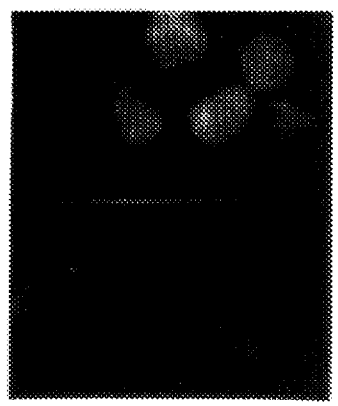

In the present Example, erythroblasts (transformed by an EGF-receptor retrovirus, Khazaie et al. 1988) were incubated for 18 hours in a transferrin-free differentiating medium (composition in Zenke et al. 1988) at 37° C. (cell concentration 1.5×10$^6$/ml). After addition of the various transferrin-polylysine conjugates (or, as a control, the corresponding amount of sterile twice distilled water), the cells were incubated at 37° C. in the presence of 10 ng/ml EGF in order to maintain the transformed state. After 24 and 48 hours, about 5×10$^5$ cells were removed, washed once in phosphate-buffered physiological saline (PBS; pH 7.2), fixed with 50 times the volume of a mixture of 3.7% formaldehyde and 0.02% glutaraldehyde in PBS (10 minutes, 40° C.), washed once in PBS, embedded in Elvanol and examined under a fluorescence microscope (Zeiss Axiophot, Narrow Band FITC and TRITC activation). At the same time, the growth rate of the cells was determined in other aliquots of the various mixtures. 100 µl cell suspension were taken and the incorporation of $^3$H-thymidine (8 µCi/ml, 2 hours) was determined as described in Leutz et al. 1984. FIG. 5 shows that the erythroblasts incubated with transferrin-polylysine show 2 to 10 strongly fluorescing vesicles after 24 hours, which cannot be detected in the controls. Table A shows that, with the exception of fraction 6, all the conjugates have been absorbed by virtually all the cells.

FIG. 5 shows fluorescence images of chicken erythroblasts which have been incubated for 24 hours without (A) or with FITC-labelled transferrin-polylysine conjugates (B,C). When they are activated with blue light (B, in order to detect FITC), significantly more fluorescing vesicles can be detected in each cell. The specificity of this fluorescence is shown by the fact that the vesicle fluorescence does not occur when activated with green light (C: at which a similar non-specific fluorescence of the cells can be seen as in A) (C).

The fact that the cells grow equally rapidly in all the samples (as measured by the incorporation of tritiated thymidine ($^3$H TdR), Table A) shows that the cells are not dimensioned by the polylysine constructs and consequently non-specific uptake (e.g. through cell membranes which have become permeable) can be ruled out.

EXAMPLE 6

The objective of the tests carried out in this Example was to show that the transferrin-polylysine conjugates used here are used by the cell in the same way as native transferrin, i.e. they pass through the normal transferrin cycle with similar efficiency. Erythroblasts which can be induced to mature into normal erythrocytes by "switching off" the transforming oncogene are particularly suitable as a test system for this purpose (Beug et al, 1982). The literature shows that for normal maturation such cells require high concentrations of transferrin-iron complex (100 to 200 µg/ml, 3 times lower concentrations prevent the cells from maturing and will result in the death of the cells after several days (Kowenz et al. 1986)). It has also been shown (Schmidt et al 1986) that recycling, i.e. the reuse of transferrin receptors and hence a transferrin cycle proceeding at optimum speed are indispensible for normal in vitro differentiation.

Erythroblasts (transformed by the EGF-receptor retrovirus) were induced to differentiate by the removal of EGF and the addition of an optimum amount of partially purified chicken erythropoietin (Kowenz et al., 1986, free from transferrint. Incubation was carried out at a cell concentration of 1×10$^6$/ml in transferrin-free differentiating medium at 42° C. and 5% $CO_2$. A t the start of incubation, either native transferrin-iron complex (Sigma, 100 µg/ml) was added or the iron-saturated transferrin-polylysine conjugates were added (concentration again 100 µg/ml). The growth and maturity of the cells were analysed are 24 and 48 hours by the following methods:

1. by determining the number of cells (using a Coulter Counter, Model ZM, Beug et al. 1984)
2. by recording cell size distributions (using a Coulter Channelyzer Model 256) and
3. by photometric determination of the haemoglobin content of the cells (Kowenz et al., 1986).

In addition, aliquots of the mixtures were centrifuged after 72 hours in a cytocentrifuge (Shandon) on an object carrier and subjected to histochemical investigation t o detect haemoglobin (staining with neutral benzidine plus Diff-Quik rapid staining for blood cells, Beug et al 1982).

The results in Table B clearly show that cells which were induced to differentiate in the presence of the polylysine-transferrin conjugates fractions 1 to 5 mature just as efficiently and as fast as those which were incubated with native transferrin-iron. The cells in the transferrin-free controls, on the other hand, showed a much slower cell growth and accumulated only small amounts of haemoglobin. Investigation of cell phenotype on stained cytospin preparations showed that the cells incubated with polylysine-transferrin conjugates were matured into late reticulocytes (late reticulocytes, Beug et al., 1982) in just the same way as those which had been treated with native transferrin, whereas the cells incubated without transferrin constituted a mixture of disintegrated and immature cells resembling erythroblasts (Schmidt et al. 1986). Only the cells treated with transferrin-polylysine fraction 6 showed a lower haemoglobin content and a higher percentage of immature cells (Table B). This shows that fraction 6 conjugated with a particularly large amount of polylysine operates less well in the transferrin cycle. At the same time, this result indicates the sensitivity of the test method.

EXAMPLE 7

Just as in Example 6, various transferrin-polylysine conjugates and transferrin-protamine conjugates were examined for their ability to functionally replace the native transferrin-iron complex in the maturation of chicken erythroblasts into erythrocytes.

It has already been shown that terminally differentiating chicken erythroblasts demand an optimally functioning transferrin cycle; i.e. without transferrin or if the transferrin receptor recycling is inhibited, the cells die off (Kowenz et al., 1986; Schmidt et al., 1986). Since the partially purified chicken erythropoietin normally used still contains transferrin, EPO was replaced by a transferrin-free, partially purified erythroid growth factor in order to permit erythroid differentiation (REV factor; Kowenz et al., 1986; Beug et al., 1982): as target cells, erythroblasts which had been transformed with a retrovirus containing the human epidermal growth factor receptor (EGFR) together with a temperature-sensitive v-myb oncogen were replicated in CFU-E medium (Radke et al., 1982) in the presence of 20 ng/ml of EGF. These cells are activated to replicate abnormally by EGF, whilst the withdrawal of the growth factor EGF and the simultaneous addition of REV factor causes the cells to enter into normal differentiation. After being washed twice in transferrin-free medium the cells were transferred into transferrin-free medium and varying quantities of iron-saturated transferrin or transferrin-polycation conjugates were added (before or after being complexed with plasmid DNA). After 1, 2 and 3 days' incubation at 42° C. the differentiating state of the cells was determined by cytocentrifugation and histochemical staining or by quantitative haemoglobin measurement.

The results of these tests are shown in FIG. 6 or Table C.

Figure 6A:
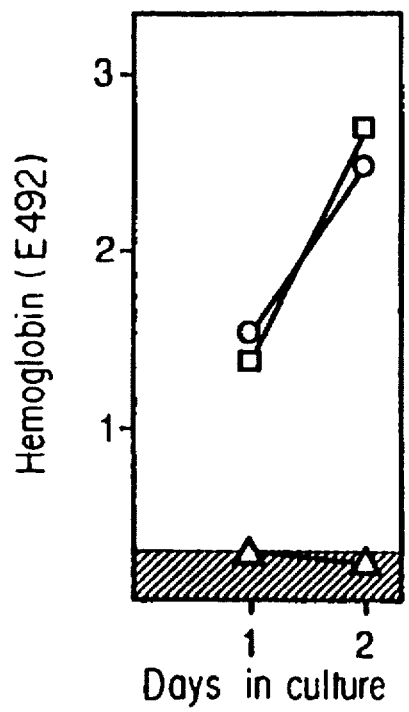
FIG. 6 (panels A and B). Erythroid differentiation as a function of the concentration of transferrin or transferrin-polylysine.

The cells ($1 \times 10^6$/ml) were added to conalbumin-free differentiating medium (Zenke et al., 1988), supplemented by 1 µg/ml of insulin and REV factor at an optimum concentration (Kowenz et al., 1986; dilution 1:5,000), once without additives (triangles), once with iron-saturated conalbumin (circles) and once with iron-saturated TfpL 270 conjugates (squares) (100 µg/ml in each case); in 14 mm dishes. After incubation for 24 and 48 hours, the haemoglobin content was photometrically determined in 100 µl aliquots. The shaded area shows the haemoglobin content of cells grown without transferrin (average from 4 measurements; FIG. 6A).

Figure 6B:
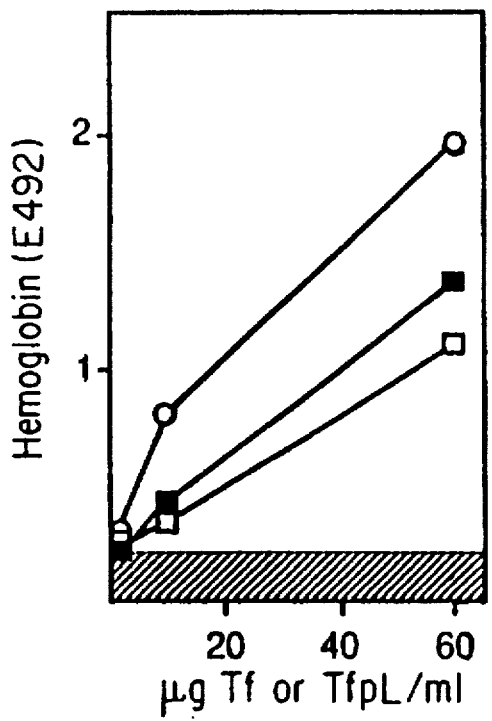

In order to analysis the erythroid differentiation as a function of the concentration of transferrin or transferrin-polylysine, the cells were placed in medium containing the specified amounts of iron-saturated conalbumin (open circles), TfpL 90 (open squares) or TfpL 270 (solid squares) as described above and after 2 days the haemoglobin content was determined photometrically (FIG. 6B).

Table C

The erythroid differentiation was monitored by photometric haemoglobin measurement (see FIG. 6), by counting in a Coulter counter or by cytocentrifugation and subsequent neutral benzidine staining (to determine the haemoglobin) plus histological dyes (Diff Quik; Beug et al., 1982b). The final concentrations of transferrin and transferrin.conjugates in test 1 were 60 µg/ml; in tests 2 and 3 they were 100 µg/ml. The DNA concentration in test 2 was 10 µg/ml. The proportion of disintegrated cells, mature cells (LR: late reticulocytes; E: erythrocytes) and immature cells (Eb1) was determined using the methods described by Beug et al., 1982b and Schmidt et al., 1986. The results obtained show that two different transferrin-polylysine conjugates (TfpL90 or TfpL270) as well as the transferrin-protamine conjugate are capable of functionally replacing native transferrin, by ensuring the rapid transfer of iron into differentiating red cells, the specific activity thereof being 1.5 to 2 times lower (cf. FIG. 6). The complexing of DNA with transferrin-polylysine 270 and transferrin protein did not materially alter the biological activity of the conjugates. In a control experiment it was established that, when polylysine or protamine is added, mixed with a suitable quantity of iron citrate instead of the transferrin conjugates, the cells were unable to differentiate and died off, just like the cells in the comparison samples which had been incubated without transferrin.

All in all, the tests according to Examples 6 and 7 have shown that both types of polycation-transferrin conjugates transported iron only slightly less efficiently than natural transferrin.

EXAMPLE 8

Polylysine-transferrin conjugates make it possible for DNA to be absorbed into chicken erythroblasts.

The present Example was intended to investigate whether DNA of a size corresponding to that of tDNA ribozymes (see FIG. 7) is capable of being efficiently transported into the interior of the cell by transferrin-polylysine conjugates. In the present Example, tDNA with an insert of the sequence CGTTAACAAGCTAACGTTGAGGGGCAT-
GATATCGGGCC CCGGGCAATTGTTCGATTG-
CAACTCCCCGTACTATAGC molecular weight about 300,000 was used, terminally labelled with gamma 32P ATP (Maniatis). About 0.3 µg of this DNA, dissolved in 20 µl of TE buffer were mixed either with 10 µg of native transferrin, with 10 µg of transferrin-polylysine conjugate fraction 3, in each case dissolved in 50 µl of twice distilled water plus 400 µg/ml of bovine serum albumin (Beug H., et al., 1982) or with 50 µl of this solvent without transferrin. The DNA protein mixtures were each added to 2 ml of transferrin-free differentiating medium, $4 \times 10^6$ chicken erythroblasts were added (which had previously been transformed with an EGF receptor retrovirus and preincubated for 18 hours in transferrin-free medium in the presence of EGF (Khazaie K., et al., 1988) and the mixtures were incubated for 8 hours at 37° C. and 5% $CO_2$. Then the cells were centrifuged off, the supernatant was removed and the cells were washed 3 times in transferrin-free medium. Cell sediment and culture medium were taken up in 1% SDS, 1 mg/ml of proteinase K, 300 mM NaCl, 20 mM tris pH 8.0, 10 mM EDTA (PK/SDS buffer), incubated for 30 minutes at 37° C., extracted with phenol/chloroform, and the DNA isolated by ethanol precipitation. Isolated DNA with a radioactivity of 2000 cpm in all were separated on a non-denaturing 3.5% acrylamide gel (TBE, Maniatis) and the DNA was detected by autoradiography. It was shown that, in the cell sample treated with transferrin-polylysine, approximately 5 to 10 times more DNA had been absorbed by the cells than in the control samples with native transferrin.

EXAMPLE 9

Polylysine-transferrin conjugates make it possible for plasmid-DNA to be absorbed into and expressed in chicken erythroblasts.

In these tests, plasmid-DNA containing the *Photinus pyralis* luciferase gene as reporter gene was used to investigate gene transfer and expression. For this purpose, pRS-Vluc plasmid DNA (De Wet, J. R., et al., 1987) was prepared using the Triton-X lysis standard method (Maniatis), followed by CsCl/EtBr equilibrium density gradient centrifugation, decolorising with butanol-1 and dialysis with 10 mm Tris/HCl, pH 7.5, 1 mm EDTA. In a typical complex forming reaction, 10 µg of transferrin-polylysine or transferrin-protamine conjugates were slowly added, with careful stirring, to 3 µg of pRSVluc plasmid DNA contained in 250 µl of 0.3M NaCl (it was established that these conditions are adhered to, up to 100 µg of transferrin-polycation conjugate and 30 µg of plasmid-DNA can be used in a final volume of 500 µl without precipitation of the conjugate/DNA complexes). After 30 minutes at ambient temperature, the complexes were added directly to 5–10× $10^6$ HD3 cells (0.5–1×$10^6$ cells per ml, EBM+H medium (Beug et al., 1982a; 37° C., 5% $CO_2$) and the mixtures were incubated for 16 to 48 hours (the cell line used was the ts-v-erbB transformed chicken erythroblast cell line HD3). The cells were harvested (5 min at 1500×g, 4° C., washed twice with phosphate-buffered saline (PBS) and taken up in 100 µl of 0.25M tris/HCl, pH 7.5. Cell extracts were prepared by three cycles of freezing and thawing, followed by high-speed centrifugation (15 min, 18,500×g, 4° C.). Aliquots of these cell extracts were examined for the presence of luciferase enzyme activity (De Wet, J. R., et al., 1987). The bioluminescence was measured using clinilumate (Berthold, Wildbach, BRD). It was established that the presence of the transferrin-polycation/DNA complexes in the culture medium does not have any harmful effects on cell growth or replication. As can be seen from FIG. 8, maximum luciferase activity was achieved when using 3 µg of DNA/10 µg of TfpL and 0.3–1 µg of DNA/Tfprot. Assuming that all the conjugate/DNA complexes formed were identical, this corresponds to a molar ratio of 25 or 75 conjugate molecules per molecule of plasmid DNA. It can be concluded from this that the DNA in the complex is entirely covered by the conjugate molecules, and indeed at a conjugate/DNA ratio which obviously guarantees electroneutrality (calculated on the basis of the positive charges in the polycation which are necessary in order to neutralise the negative charges of the phosphate groups in the DNA). This assumption agrees with the observation that, compared with transferrin-polylysine, three times more transferrin/protamine, less strongly positively charged, is required for optimum complex forming and gene transfer. This assumption also accords with the results for the conjugate/DNA ratio obtained in Example 4 required for efficient complex formation.

The sensitivity of this gene transfer system was determined using a TfpL/DNA ratio which had been adjusted to the optimum for complex forming. The results of these tests are shown in FIG. 9: less than 1 ng of plasmid DNA coding for luciferase still shows a detectable signal. The use of more than 2 µg of plasmid DNA, complexed with 6 µg of TfpL or 20 µg of Tfprot, does not result in any further increase in luciferase activity, presumably because the system is saturated. It was also found that no special concentration of salt or ions is needed for the complex forming, since TfpL/DNA complexes formed at various salt concentrations (0, 20, 50 100, 200 mM NaCl) prove to be equally effective in gene transfer experiments. (FIG. 8 and FIG. 9: circles indicate Tfprot, squares indicate TfpL). It was possible to demonstrate that the absorption of transferrin-polycation/DNA complexes into the cells was effected via the transferrin receptor. First of all, as illustrated in FIG. 10A, it was found that the luciferase activity achieved by TfpL-DNA complexes is at least 100 times higher than the activity measured for pL-DNA complexes. A comparison test shows that a mixture of polylysine and transferrin alone did not facilitate the uptake of plasmid DNA. In another test, an excess of native transferrin was added to a constant quantity of TfpL-DNA complex. FIG. 10B shows that free transferrin in the medium efficiently competes for the DNA uptake mediated by TfpL, resulting in a reduction in the luciferase enzyme activity. From this it can be concluded that the uptake of the TfpL-DNA complexes by the cell is effected via the transferrin receptor.

EXAMPLE 10

In preliminary tests it was established, by the transfection of chicken fibroblasts with erbB cut DNA that the erbB cut ribozyme-tDNA is expressed in chicken cells.

This Example shows that tDNA ribozymes directed against the erbB oncogene can be introduced into erbB-transformed chicken erythroblasts with the aid of polylysine-transferrin conjugates and can weaken the transforming activity of the oncogene.

Two tRNA ribozyme genes, directed against the translation initiation region of erbB, were constructed (see FIGS. 7 and 11). About 100 µg of each plasmid containing the gene were digested in EcoRI in order to free the tRNA ribozyme gene on a 325 bp fragment.

The digestion products were terminally labelled by means of klenow fragment and purified by gel electrophoresis using a 2% agarose/TBE gel. The vector fragment and the tRNA-ribozyme gene fragments were located by staining with ethidium bromide, cut out and recovered by electroelution, extraction with phenol/chloroform and chloroform and ethanol precipitation. The purified, radioactively labelled DNA fragments were then used, with the aid of the transferrin-polylysine transporting system, to determine the uptake and inhibition of the erbB-RNA. The vector pSPT 18 was used as the control DNA.

The test cell system used was a chicken erythroblast cell line transformed by a temperature-sensitive mutant (ts 34, Graf et al. 1978) of the avine erythroblastosis virus AEV (Beug et al. 1982 b). The erbA oncogene which is also expressed in these cells can be inhibited by a specific protein kinase inhibitor (H 7). (It was found that the v-erbA oncogene is phosphorylated in vivo and in vitro (i.e. as a bacterially expressed protein) at two sites, namely Ser 28 and Ser29, by protein kinase C or by cAMP-dependent protein kinase. Mutation of these serines to form alanines prevents phosphorylation and destroys the v-erbA oncogene activity. H7 is a specific inhibitor of these two kinases and is capable of selectively stopping the changes caused by v-erbA (e.g. blocking of differentiation) in erythroblasts which contain v-erbA-v-erbB.)

It is known that erythroblasts in which the erbB oncogene is inactivated—e.g. by increasing the temperature in the case of a temperature-sensitive erbB mutant, are induced to mature into erythrocytes. One of the first indications of this process is the induction of haemoglobin synthesis, which can be detected by a sensitive test (acidic benzidine staining, Orkin et al, 1975, Graf et al, 1978) at the level of the single cells. Thus, a specific increase in the number of benzidine-positive cells might be expected, as a phenotypical effect of a ribozyme directed against erbB in this test system.

The test series on which this Example is based was carried out as follows: the various DNA preparations (see above and Table D), dissolved in 30 μl of TE buffer, were mixed with 10 μg of native transferrin-iron complex or transferrin-polylysine conjugate (dissolved in 50 μl of twice distilled water) and then incubated for 30 minutes at 37° C.

In the case of the vector DNA (10 μg), correspondingly more (100 μg) of the transferrin preparations was used. The DNA transferrin-DNA mixtures were added to 1 ml of transferrin-free differentiating medium (Zenke et al., 1988). The test cells (per batch 3×10⁶) were incubated before the test for 60 minutes in transferrin-free differentiating medium at 42° C. (to intensify the uptake of transferrin) and added to the DNA-transferrin-containing mixtures. After 6 hours, 18 hours and 68 hours (see below for treatment of cells), samples were taken as described, separated into supernatant and cell sediment, taken up in PK/SDS-buffer and the DNA was analysed.

FIG. 12 shows that, analogously to Example 8, in the cell sample treated with transferrin-polylysine, about 5–10 times more DNA was absorbed by the cells than in the control samples with native transferrin.

Trace m: molecular weight marker: pBR322 DNA, cleaved with HpaII and radioactively labelled using the klenow fragment of DNA polymerase with alpha-$^{32}$P-CTP (Maniatis)

Trace 1: 2000 cpm ES13 fragment

Trace 2: material from cells treated with transferrin and ES13

Trace 3: material from cells treated with transferrin-polylysine and ES13

After the end of incubation (6 hours) the cells were centrifuged off and incubated in transferrin-containing differentiating medium with erythropoietin and insulin (Kowenz et al, 1986, Zenke et al 1988, 2 ml per batch and at 37° C., i.e. in the presence of an active v-erbB protein) for a further 72 hours.

The following results were obtained

1. As in Example 8, an increased uptake of DNA could be observed in the size of the erbB cut DNAs in the cell samples treated with transferrin-polylysine (about a 5-fold increase).

2. Table D shows that in every case where erbB cut ribozyme tDNA was introduced into erbB transformed erythroblasts with the aid of polylysine-transferrin constructs, the percentage of benzidine-positive cells was significantly increased (approximately doubled) (the standard used was the samples treated with vector DNA in which the use of polylysine-transferrin conjugates, as expected, did not lead to any increase in the number of benzidine-positive cells).

EXAMPLE 11

Efficient binding and internalisation of transferrin-polylysine/DNA complexes in haematopoietic chicken cells.

The binding of TfpL and TfpL-DNA to cell surface receptors was measured with tritium-labelled substances using the method described by Stein et al., 1984. $^3$H-labelled TfpL was prepared by conjugation of labelled polylysine with transferrin using the method described in Example 1. The labelling of polylysine 90 was carried out by treating with formaldehyde and $^3$H-labelled sodium borohydride (Ascoli and Puet, 1974). The results of these tests are shown in FIG. 13. Labelled TfpL 90 (squares) or labelled TfpL 90 complexed with pB-SK- DNA (Promega Biotech, prepared by Triton-X lysis. CSCl/EtBr equilibrium density gradient centrifugation, decolorisation with 1-butanol and dialysis against 10 mM Tris/HCl pH 7.5, 1 mM EDTA) (triangles) were investigated for their specific binding to the transferrin receptor of HD3 cells. For this purpose the conjugates or complexes (0.1–100 nM) were added to HD3 cells (1×10⁶/ml in MEM (Eagle's Minimum Medium)+1% BSA) and incubated for 3 hours. FIG. 13 shows that both the conjugates and also the complexes bind to HD3 cells in such a way that saturation occurs. The apparent binding constants calculated from these data amounted to 22 nM for TfpL and 43 nM for TfpL-DNA complexes. Although somewhat higher, these values correspond relatively well to those obtained for native transferrin, which were found to be 15 nM.

In order to monitor the uptake of TfpL-DNA complexes into intracellular vesicles, first of all HD3 cells were incubated at 37° C. for 18 hours with transferrin-free differentiating medium. After the addition of FITC transferrin or TfpL conjugates (labelled with FITC at the polylysine group, and complexed with DNA in some experiments), the cells were incubated for a further 18 hours. The cells were cytocentrifuged, fixed with a mixture of 3.7% formaldehyde and 0.02% glutaraldehyde, washed with PBS, embedded in Mowiol 4.88 and examined under a Zeiss Axiophot Fluorescence Microscope. The control used consisted of FITC-labelled goat anti-mouse antibodies (0.1 mg/ml) (see Example 5). For quantitative determination of FITC-Tf, FITC-TfpL and FITC-TfpL/DNA, the cells were incubated for 6 hours with the preparation in question (Tf: 40 μg/ml; TfpL270: 50 μg/ml; TfpL270f plus pB-SK-DNA (Promega Biotech, prepared by Triton-X lysis, CSCl/EtBr equilibrium density gradient centrifugation, decolorising with 1-butanol and dialysis against 100 mM Tris/HCl pH 7.5, 1 mM EDTA): 50 μg/ml or 16 μg/ml; binding buffer), washed 3 times in cold PBS/BSA and subjected to quantitative FACS analysis in a Becton-Dickinson (BD) FACSAN.

FIG. 14 shows that both with TfpL and with TfpL-DNA, all the cells have a relative fluorescence increased more than 10 times, indicating that the conjugates or complexes have been taken up by more than 95% of the cell s (Tf: . . . ; TfpL: . . . ; TfpL/DNA:__; binding buffer:_).

EXAMPLE 12

Expression of DNA absorbed into the cell by means of TfpL

After it had been established in the preceding Examples that the gene transfer with TfpL is not harmful to cell growth, the activity of TfpL-DNA complexes which were used themselves for a longer period of time was tested (the DNA used was plasmid DNA containing the luciferase gene, as described in Example 9). In this test, the same concentration of HD3 cells was incubated for 1 to 4 days with or without daily supplementing with TfpL-DNA complexes.

At various intervals of time, aliquots were investigated for lucerifase enzyme activity, as described in Example 9. In the cultures with repeated addition of the complexes, a relatively high level of luciferase gene expression was measured (100,000 to 200,000 light units per $10^7$ cells), which remain substantially constant throughout the entire observation period. During this period, no cytotoxic effects were observed. If cells were charged with the complexes only once, the luciferase activity decreased between the 2nd and 4th days by a factor of 10 to 20. These results show that in spite of the obviously transient expression of the luciferase gene, introduced into the cell with the aid of the conjugates according to the invention, a constantly high expression of the introduced genes can be maintained by repeated addition.

EXAMPLE 13

In order to establish how large a proportion of cells actually express plasmid DNA introduced by transferrin infection, HD3 cells were incubated with TfpL/DNA complexes as described in the preceding Examples. pRSV-βGal plasmid DNA (___) was used as the DNA. The expression of this reporter gene was then investigated in individual cells by FACS analysis (Nolan et al., 1986). TfpL-pB-SK-DNA ( . . . ) was used as the control. The fluorescence βGal substrate FDG (fluorescene-Di-β-d-galactopyranoside) was introduced by osmotic shock and the distribution of cells containing fluorescene which was released from FDG by the βGal enzyme activity was investigated. Uniform distribution of fluorescene-containing cells leads to the conclusion that a large proportion of cells express the βGal reporter gene. The results of these tests are shown in FIG. 15.

BIBLIOGRAPHY

Ascoli, M. and Puett, D. (1974), Biochem. Biophys. Acta 371, 203–210.
Beug, H., et al., (1982a), J. Cell Physiol. Suppl. 1, 195–207.
Beug, H., et al., (1982b), Cell 28, 907–919.
Beug, H., et al. (1984), Cell 36, 963–972.
Cormier et al., (1988), Nucleic Acids Res. 16, 4583.
Deakin, H., et al., (1963), Biochem. J. 89, 296.
Felsenfeld et al., (1978), Nature 271, 115–122.
Graf et al., (1978), Nature 275, 496–501.
Heubers et al., (1987), Physiol. Rev. 67, 520–582.
Jung et al., (1981), Biochem. Res. Commun. 101, 599.
Kahazaie, K., et al., (1988), EMBO J., 10, 3061–3071.
Killisch, I., et al., (1990), In Preparation
Kowenz, E., et al., (1986), Mod. Trends in Human Leukemia VII, Springer Verlag, pp. 199–209.
Lemaitre et al., (1987), Proc. Natl. Acad. Sci. 84, 648.
Maniatis et al., Molecular Cloning. Cold Spring Harbor 1982
Morvan et al., (1988) Nucleic Acids Res. 16, 833.
Nolan, G. P., et al., (1986), Proc. Natl. Acad. Sci. 85, 2603–2607
Praseuth et al., (1988), Proc. Natl. Acad. Sci. 85, 1349.
Orkin, et al., (1975), Proc. Natl. Acad. Sci. 72, 98–102.
Radke, K., et al., (1982), Cell 31, 643–653.
Schmidt et al., (1986), Cell 46, 41–51.
Smith et al., (1986), Proc. Natl. Acad. Sci. 83, 2787.
Stein et al., (1984), J. Biol. Chem. 259, 14762–14772.
Stein et al., (1988), Nucleic Acids Res. 16, 3209.
Stirchak et al., (1987), J. Org. Chem. 52, 4203.
Warrant R. W., et al., (1978), Nature 271, 130–135.
Wu, G. Y., et al., (1988), J. Biol. Chem. 263, 14621–14624.
Zamecnik et al. (1986), Proc. Natl. Acad. Sci. 83, 4143.
Zenke, M., et al., (1988), Cell 52, 107–119.

TABLE A

Transporting of Polylysin-transferrin into erythroblasts

| Batch | Medium | Transferrin-polyLysin | Vesicle fluorescence 24 h | Vesicle fluorescence 48 h | Viability (3H Td R-incorporation) 48 h |
|---|---|---|---|---|---|
| 1 | 2 ml | without addition | <1% | <1% | 140.000 cpm |
| 2 | 2 ml | 145 µl H₂O | <1% | <1% | 126.000 cpm |
| 3 | 2 ml | 145 µl TfpL Fr1 | >90%++ | >90%++ | 137.000 cpm |
| 4 | 2 ml | 145 µl TfpL Fr2 | >90%+++ | >90%+++ | 161.000 cpm |
| 5 | 2 ml | 145 µl TfpL Fr3 | >90%+++ | >90%+++ | 153.000 cpm |
| 6 | 2 ml | 145 µl TfpL Fr4 | ca. 80%+++ | >90%+++ | 151.000 cpm |
| 7 | 2 ml | 145 µl TfpL Fr5 | ca. 60%+++ | >90%+++ | 153.000 cpm |
| 8 | 2 ml | 145 µl TfpL Fr6 | ca. 40%+++ | >90%+++ | 165.000 cpm |

++ and +++ indicate the relative intensity of the vesicle fluorescence

TABLE B

PolyLysin-Transferrin can functionally replace normal Transferrin in the stimulation of the in vitro-induced maturation of erythroblasts

| No | Medium | Addition[b] | No of cells (× 10⁶/ml) 24 h | No of cells (× 10⁶/ml) 48 h | Hemoglobin E 492 24 h | Hemoglobin E 492 48 h | Degree of maturity % reticulocytes 72 h |
|---|---|---|---|---|---|---|---|
| 1 | 2 ml | Fe-Transferrin | 3,28 | 4,38 | 1,38 | 2,74 | >80% |
| 2 | 2 ml | — | 2,62 | 2,56 | 0,35 | 0,23 | <1% |
| 3 | 2 ml | H₂O | 2,60 | 2,42 | 0,30 | 0,13 | <1% |
| 4 | 2 ml | TfpL Fr1 | 3,70 | 4,44 | 1,36 | 2,69 | >80% |
| 5 | 2 ml | TfpL Fr2 | 3,56 | 4,24 | 1,16 | 2,51 | n.b.[a] |
| 6 | 2 ml | TfpL Fr3 | 3,72 | 4,54 | 1,58 | 2,54 | >80% |
| 7 | 2 ml | TfpL Fr4 | 3,48 | 4,56 | 1,57 | 2,55 | n.b. |
| 8 | 2 ml | TfpL Fr5 | 3,36 | 4,26 | 1,41 | 2,47 | n.b. |
| 9 | 2 ml | TfpL Fr6 | 3,58 | 4,4 | 1,14 | 1,93 | 60–65% |

[a]: not determined
[b]: Fe-Transferrin, 200 µg in 13 µl; TfpL- fraction 200 µg in 130 µl; H₂O, 130 µl

TABLE C

| Test | Medium- Addition Transferrin | Transferrin Conjugate | DNA | Cell number (× $10^6$/ml) | Hb ($E^{492}$) | % desint. Cells | % LR + E | % Ebl |
|---|---|---|---|---|---|---|---|---|
| 1 | − | — | — | 2.56 | 0.259 | 56 | <1 | 44 |
|   | + | — | — | 3.72 | 1.997 | 3 | 73 | 1 |
|   | − | Tfp190 | — | 3.67 | 1.105 | 5 | 54 | 8 |
|   | − | Tfp1270 | — | 3.30 | 1.366 | 11 | 60 | 4 |
| 2 | − | — | pRSVLuc | 1.24 | 0.28 | | n.n. | |
|   | + | — | pRSVLuc | 5.22 | 2.459 | | n.n. | |
|   | − | Tfp190 | pRSVLuc | 4.46 | 2.265 | | n.n. | |
| 3 | − | — | — | 2.1 | 0.222 | 79 | <1 | 21 |
|   | + | — | — | 2.55 | 1.369 | 6 | 72 | 0 |
|   | − | Tfp190 | — | 2.64 | 1.016 | 10 | 56 | 7 |
|   | − | Tf-Prot | — | 2.76 | 1.055 | 9 | 72 | 4 |

TABLE D

Maturation (hemoglobin content) of v-erbB - transformed erythroblasts which have absorbed v-erbB - ribozyme DNA

| | DNA | | | Transferrin | | Hemoglobin content (% positive of the acetic benzidine staining) | |
|---|---|---|---|---|---|---|---|
| No | Type | MW | Amount | Type | Amount | 14 h | 62 h |
| 1 | erb-cut 13 | $2 \times 10^5$ | 1 μg | Tf | 10 μg | <1 | 15 +− $3^a$ $(3)^b$ |
| 2 | erb-cut 13 | | | TfpL Fr5 | 10 μg | <1 | 37 +− 4 (2) |
| 3 | erb-cut 53 | $2 \times 10^5$ | 1 μg | Tf | 10 μg | <1 | 25 +− 2 (2) |
| 4 | erb-cut 53 | | | TfpL Fr5 | 10 μg | <1 | 42 +− 1 (2) |
| 5 | Vector without ribozyme | $2 \times 10^6$ | 10 μg | Tf | 100 μg | <1 | 23 +− 3 (2) |
| 6 | Vector without ribozyme | | 10 μg | TfpL Fr5 | 100 μg | <1 | 22 +− 2 (2) |
| 7 | erb-cut 13 | 53 s.o. | 0.5 + 0.5 μg | Tf | 10 μg | <1 | 21 +− 2 (2) |
| 8 | erb-cut 13 | 53 | 0.5 + 0.5 μg | TfpL Fr5 | 10 μg | <1 | 38 +− 2 (2) | a: more than 200 cells were counted out for each measurement values + or − standard deviation
b: No. of independent measurements

We claim:

1. A transferrin-polycation-nucleic acid complex capable of being absorbed into a cell by transferrin receptor-mediated endocytosis, wherein said complex is soluble under physiological conditions.

2. The complex of claim 1, wherein said polycation is selected from the group consisting of protamine, synthetic homologous or heterologous polypeptides, histone, and polyethyleneimine.

3. The complex of claim 1, wherein said polycation is a histone.

4. The complex of claim 1, wherein said polycation is polylysine.

5. The complex of claim 1, wherein said polycation contains between about 20 and 500 positive charges.

6. The complex of claim 1, wherein the molar ratio of transferrin to polycation is from about 10:1 to about 1:4.

7. The complex of claim 5, wherein the molar ratio of transferrin to polycation is from about 10:1 to about 1:4.

8. The complex of claim 1, wherein said nucleic acid is capable of specifically inhibiting expression of one or more genes.

9. The complex of claim 1, wherein said nucleic acid is capable of specifically inhibiting RNA function.

10. The complex of claim 1, wherein said nucleic acid is capable of inhibiting a viral nucleic acid.

11. The complex of claim 1, wherein said nucleic acid is capable of inhibiting one or more oncogenes.

12. The complex of claim 1, wherein said nucleic acid is capable of inhibiting one or more genes which control cell growth or differentiation.

13. The complex of claim 1, wherein said nucleic acid is a ribozyme or a gene encoding said ribozyme.

14. The complex of claim 13, wherein said complex further comprises a carrier RNA or a gene encoding said carrier RNA.

15. The complex of claim 1, wherein said nucleic acid comprises a ribozyme gene located within a carrier gene, and said carrier gene encodes tRNA.

16. The complex of claim 1, wherein said nucleic acid comprises an antisense oligonucleotide.

17. The complex of claim 16, wherein said nucleic acid further comprises a carrier nucleic acid.

18. The complex of claim 16, wherein said nucleic acid comprises a gene encoding a carrier nucleic acid.

19. A process for introducing nucleic acids into human or animal cells by transferrin receptor-mediated endocytosis comprising:

(a) providing a complex which is soluble under physiological conditions, wherein said complex comprises a transferrin-polycation conjugate and one or more nucleic acids, and (b) contacting said complex with said cells;

wherein contacting said complex with said cells occurs in vitro and said nucleic acids are expressed in said cells.

20. The transferrin-polycation-nucleic acid complex as claimed in claim 1, wherein said polycation is not a histone.

* * * * *